United States Patent
Pisharodi

(10) Patent No.: US 12,194,206 B2
(45) Date of Patent: Jan. 14, 2025

(54) EXPANDABLE SYSTEM FOR PURIFICATION AND DISINFECTION OF AIR

(71) Applicant: Madhavan Pisharodi, Brownsville, TX (US)

(72) Inventor: Madhavan Pisharodi, Brownsville, TX (US)

(73) Assignee: PERUMALA HOLDINGS, LLC, Brownsville, TX (US)

(*) Notice: Subject to any disclaimer, the term of this patent is extended or adjusted under 35 U.S.C. 154(b) by 0 days.

(21) Appl. No.: 18/328,463

(22) Filed: Jun. 2, 2023

(65) Prior Publication Data

US 2023/0302188 A1    Sep. 28, 2023

Related U.S. Application Data

(63) Continuation-in-part of application No. 18/058,185, filed on Nov. 22, 2022, now Pat. No. 11,951,164, (Continued)

(51) Int. Cl.
*A61L 9/20* (2006.01)

(52) U.S. Cl.
CPC ........... *A61L 9/20* (2013.01); *A61L 2209/12* (2013.01); *A61L 2209/14* (2013.01); *A61L 2209/16* (2013.01)

(58) Field of Classification Search
None
See application file for complete search history.

(56) References Cited

U.S. PATENT DOCUMENTS 3,105,733 A * 10/1963 Potapenko ............... F24F 3/16 422/121
3,721,072 A    3/1973 Miller
(Continued)

FOREIGN PATENT DOCUMENTS

| BG | 3818 U1 | * | 7/2020 |
| CN | 105757840 A | * | 7/2016 |
| KR | 20120007493 U | * | 10/2012 |

OTHER PUBLICATIONS

Document titled A Labyrinth Type Air Purifier, machine translation of CN 105757840 provided by Clarivate, original document published Jul. 13, 2016 (Year: 2016).*
(Continued)

*Primary Examiner* — Holly Kipouros
(74) *Attorney, Agent, or Firm* — D'Ambrosio & Menon, PLLC; Usha Menon

(57) ABSTRACT

A universal expandable system for purification and disinfection of air and methods of its use, and in particular to a system and apparatus that eliminates harmful airborne particles and microorganisms from ambient air as it passes through the system, so as to prevent the organisms and particles from entering the body of an individual user of the system. An air purification and disinfection device that is a major component of the system includes a housing having at least one disinfection chamber. Each disinfection chamber has a UV light source and a helical air flow diverter. Air purified and disinfected as it is passed through the device before the air flow is delivered to the user(s) of the device.

22 Claims, 28 Drawing Sheets

Related U.S. Application Data which is a continuation-in-part of application No. 17/545,822, filed on Dec. 8, 2021, now Pat. No. 11,511,013.

(60) Provisional application No. 63/401,817, filed on Aug. 29, 2022, provisional application No. 63/359,381, filed on Jul. 8, 2022, provisional application No. 63/353,369, filed on Jun. 17, 2022, provisional application No. 63/233,697, filed on Aug. 16, 2021.

(56) References Cited

U.S. PATENT DOCUMENTS

| | | | |
|---|---|---|---|
| 3,773,044 | A | 11/1973 | Wallace |
| 3,850,170 | A | 11/1974 | Cox |
| 4,580,556 | A | 4/1986 | Kondur |
| 4,742,760 | A | 5/1988 | Horstman |
| 5,656,242 | A | 8/1997 | Morrow et al. |
| 7,185,510 | B2 | 3/2007 | Lee et al. |
| 8,336,821 | B2 | 12/2012 | Shell et al. |
| 8,674,322 | B2 | 3/2014 | Kohler |
| 11,052,169 | B1 | 7/2021 | Pisharodi |
| 2006/0057020 | A1 | 3/2006 | Tufo |
| 2006/0263276 | A1 | 11/2006 | Pattee |
| 2008/0112845 | A1 | 5/2008 | Dunn |
| 2008/0173178 | A1 | 7/2008 | Metteer |
| 2010/0150793 | A1 | 6/2010 | Chan |
| 2011/0286167 | A1 | 11/2011 | Winkler |
| 2012/0128539 | A1 | 5/2012 | Gross et al. |
| 2012/0301363 | A1 | 11/2012 | Kim et al. |
| 2016/0001108 | A1 | 1/2016 | Zhou et al. |
| 2017/0266335 | A1* | 9/2017 | Al-Zeer .......... A61L 9/205 |
| 2017/0341762 | A1 | 11/2017 | Breigenzer |
| 2018/0250430 | A1 | 9/2018 | Machovina et al. |
| 2019/0009912 | A1 | 1/2019 | Matsui |
| 2019/0225509 | A1* | 7/2019 | Dhiman .......... C02F 1/325 |
| 2020/0282086 | A1* | 9/2020 | Silverman .......... A61L 9/015 |
| 2021/0100924 | A1* | 4/2021 | Li .......... A61L 9/014 |
| 2021/0222897 | A1* | 7/2021 | Sanabria .......... F24F 13/20 |
| 2022/0154953 | A1* | 5/2022 | Herskovitz .......... F24F 8/22 |
| 2022/0170652 | A1* | 6/2022 | Mathur .......... F24F 8/22 |

OTHER PUBLICATIONS

Document titled Mobile Respirator Filter Masks With UVC Sources and Electronic Control Unit, machine translation of BG3818 provided by Google, original document published Jul. 31, 2020 (Year: 2020).*

Document titled KR20120007493U The humidifier sterilizing by ultraviolet radiation, machine translation of KR20120007493U provided by Espacenet, original document published 2012 (Year: 2012).*

Talarico et al., Inactivation of Adventitious Agents by UVC Irradiation in a Plant-Based Influenza Vaccine Production Process, 2017, Bioprocessing, vol. 16 Issue 1 (Year: 2017).*

Sabbaghi et al., Inactivation methods for whole influenza vaccine production, 2019, Rev. Med. Virol., 29:e2074 (Year: 2018).*

Tsunetsugu-Yokota, Large-Scale Preparation of UV-Inactivated SARS Coronavirus Virions for Vaccine Antigen, 2008, Chapter 11 in SARS- and Other Coronaviruses, Ed. Cavanagh (Year: 2008).*

Bachmann et al., Immunogenicity of a viral model vaccine after different inactivation procedures, 1994, Med. Microbiol. Immunol., 183:95-104 (Year: 1994).*

'How a packaged system works' (Goodman) Jul. 29, 2016, [online] retrieved from <URL: https://web.archive.org/web/20160729193422/ https://www.goodmanmfg.com/resources/heating-cooling-101/how-a-packaged-system-works>.

Hankaniemi et al., Vaccine, vol. 37, Issue 40, pp. 5962-5971, (Year: 2019).

'UVC disinfects SARS CoV 2 by induction of viral genome damage without apparent effects on viral morphology and proteins' (Lo) Jul. 5, 2021, [online] retrieved from <URL: https://doi.org/10.1038/s41598-021-93231-7>.

'UV Inactivation of Rotavirus and Tulane Virus Targets Different Components of the Virions' (Araud) Feb. 3, 2020, [online] retrieved from <URL: https://doi.org/10.1128/AEM.02436-19.>.

'Irradiation of UVC LED at 277 nm inactivates coronaviruses in association to photodegradation of spike protein' (Ong) Oct. 17, 2022, [online] retrieved from <URL: https://doi.org/10.1016/j.heliyon.2022.e11132>.

'Ultraviolet a light effectively reduces bacteria and viruses including coronavirus' (Rezale) Jul. 16, 2020, [online] retrieved from <URL: https://doi.org/10.1371/journal.pone.0236199>.

'UVC-based photoinactivation as an efficient tool to control the transmission of coronaviruses' (Bhardwaj) Jun. 16, 2021, [online] retrieved from <URL: https://doi.org/10.1016/j.scitotenv.2021.148548>.

'UV C irradiation is highly efective in inactivating SARS CoV 2 replication' (Biasin) Mar. 18, 2021, [online] retrieved from <URL: https://doi.org/10.1038/s41598-021-85425-w>.

* cited by examiner

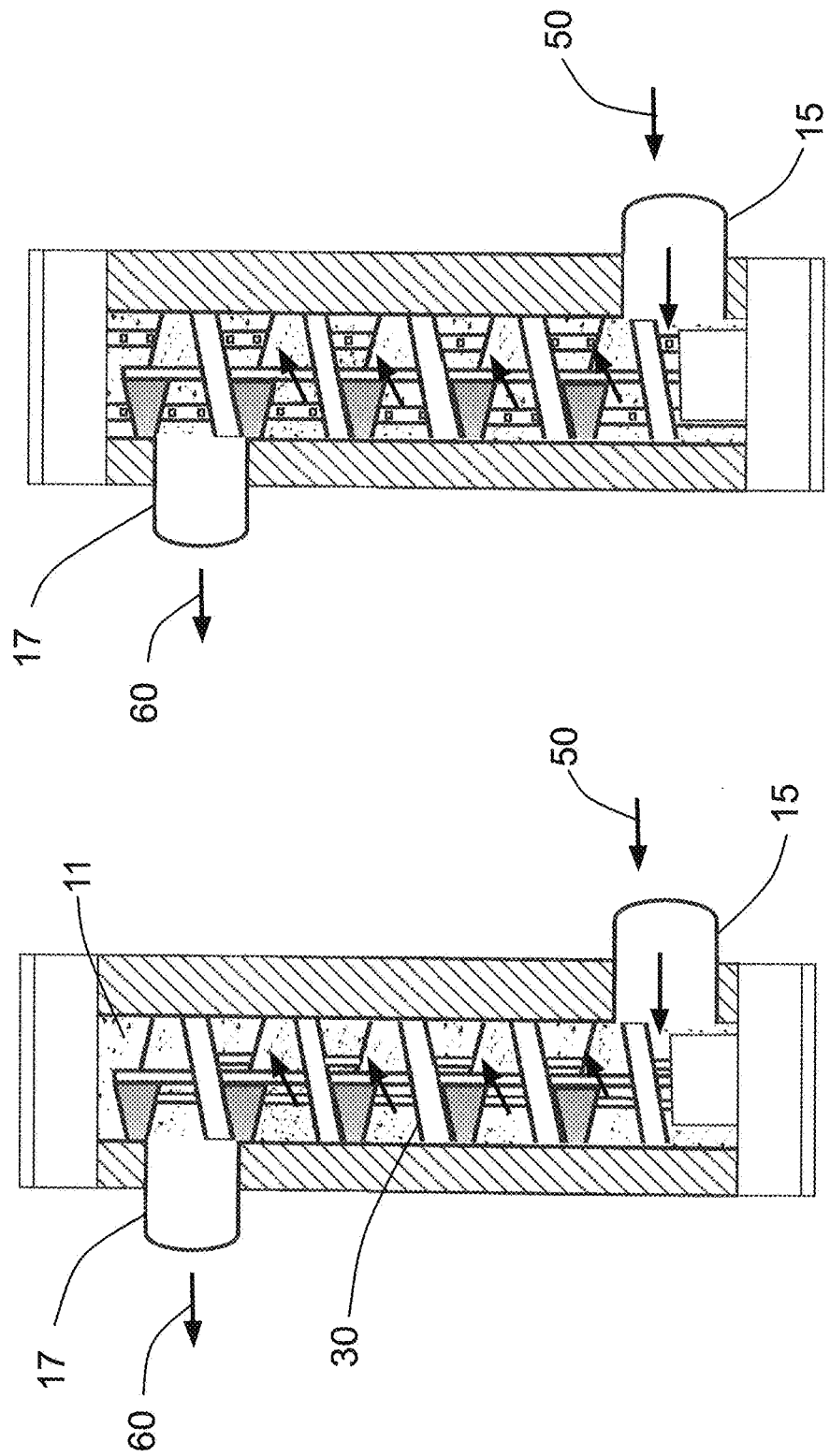

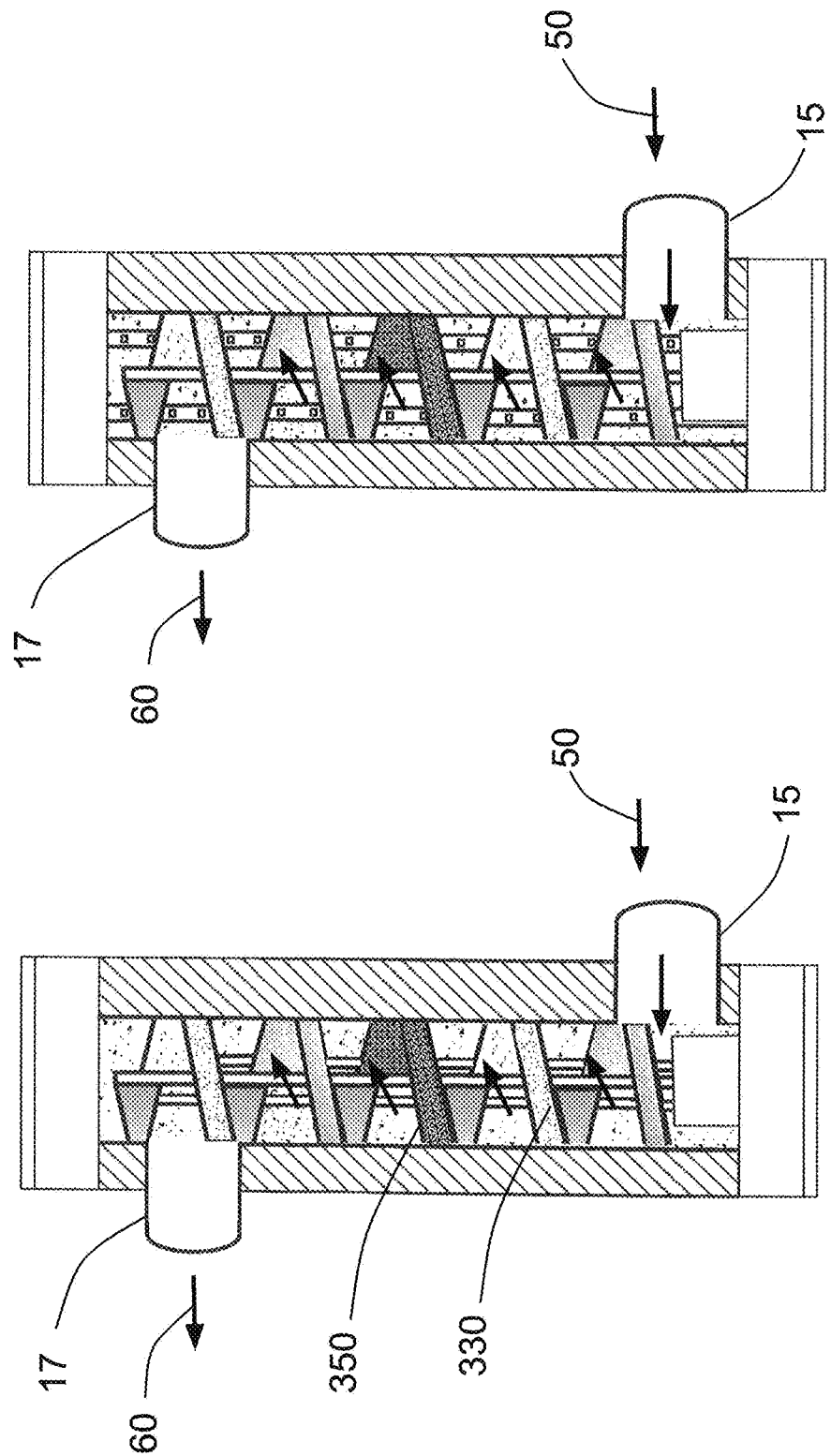

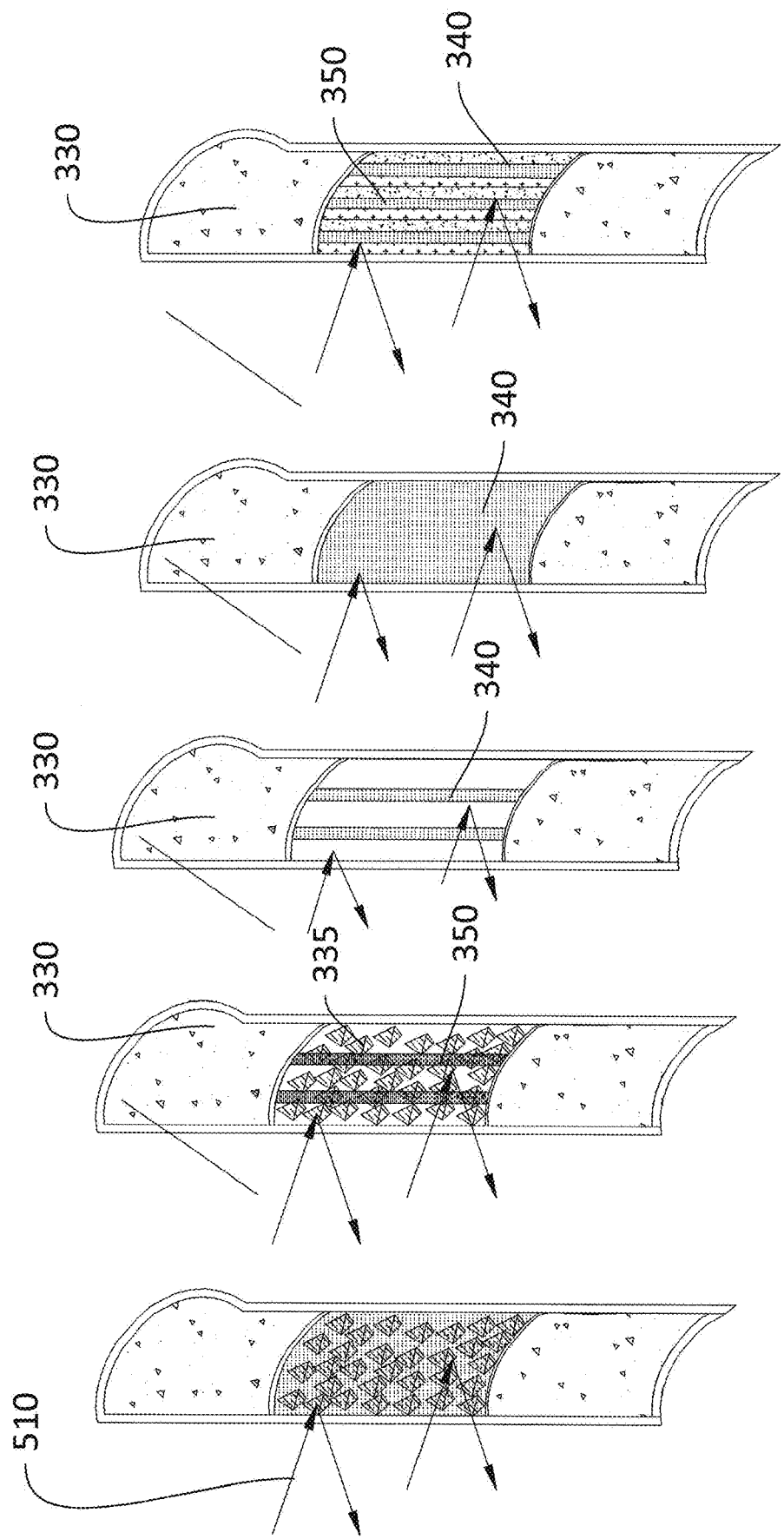

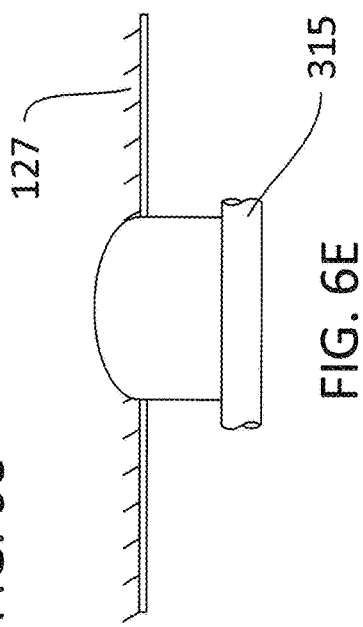
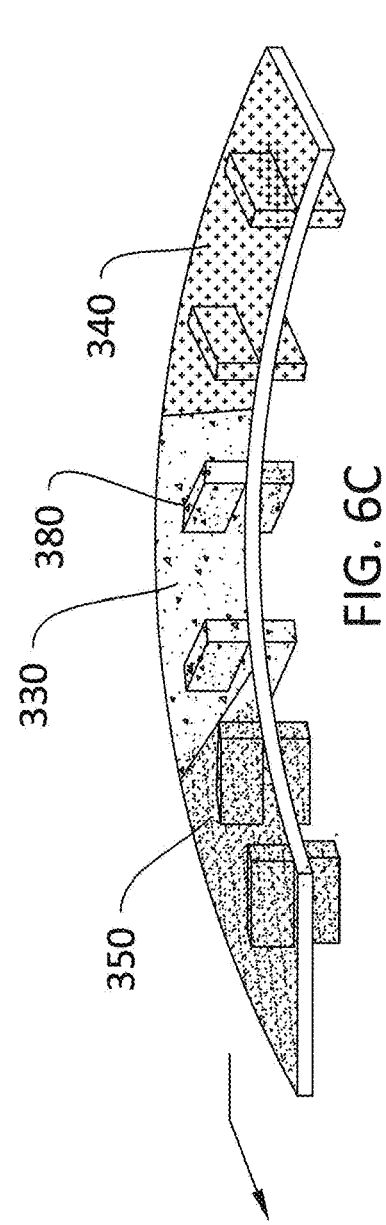
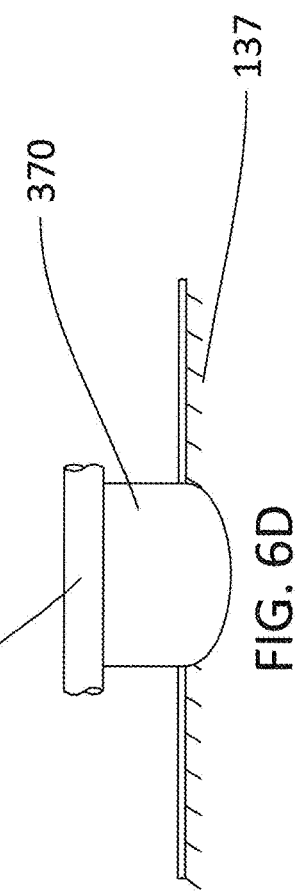
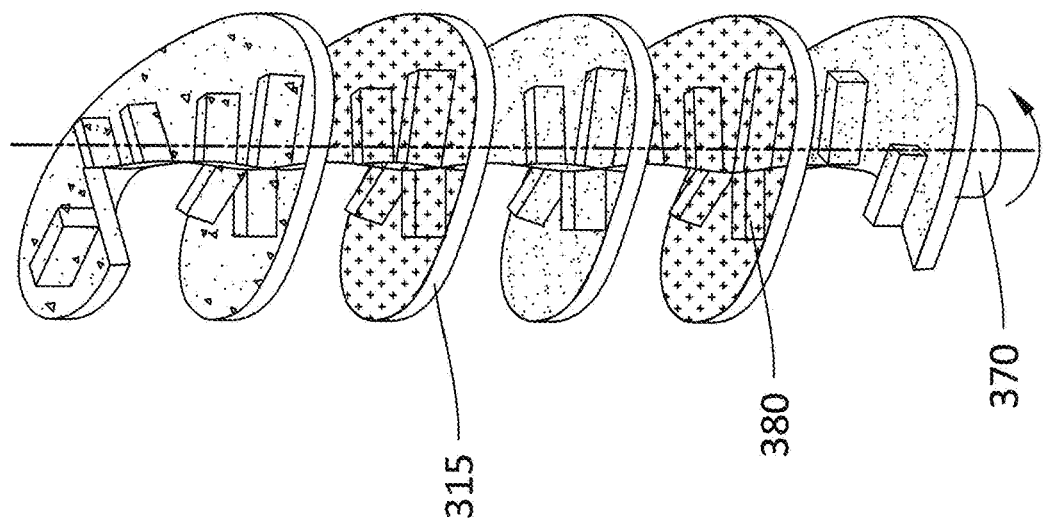

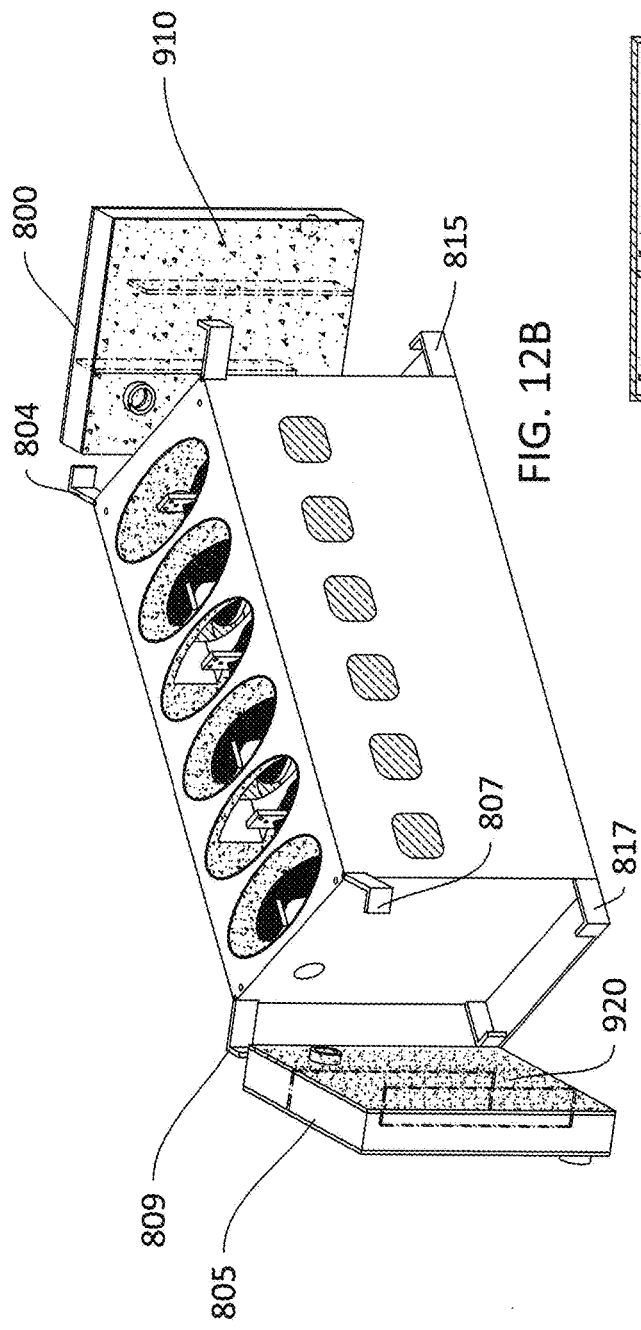
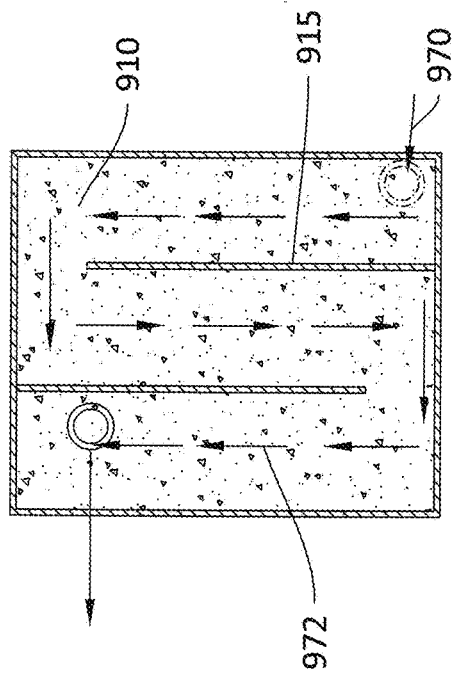
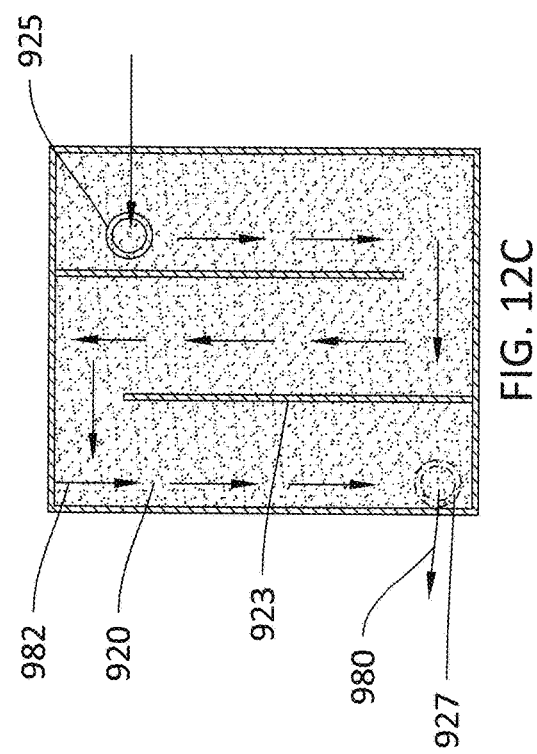
FIG. 12B
FIG. 12C
FIG. 12D

EXPANDABLE SYSTEM FOR PURIFICATION AND DISINFECTION OF AIR

CROSS-REFERENCE TO RELATED APPLICATIONS

This application claims priority to and is a continuation-in-part of U.S. Ser. No. 18/058,185 filed on Nov. 22, 2022, which claims priority to and is a continuation in part of U.S. Ser. No. 17/545,822 filed on Dec. 8, 2021, which claims priority to and is a non-provisional application of U.S. Ser. No. 63/233,697 filed on Aug. 16, 2021. This application is also a non-provisional application of and claims priority to U.S. Provisional Patent Application Ser. No. 63/353,369 filed on Jun. 17, 2022, U.S. Provisional Patent Application Ser. No. 63/359,381 filed on Jul. 8, 2022, and U.S. Provisional Patent Application Ser. No. 63/401,817 filed on Aug. 29, 2022, the entire disclosures of which are part of the disclosure of the present application and are hereby incorporated by reference in their entireties.

FIELD OF THE INVENTION

The present invention relates to systems and methods for purification and disinfection of air.

BACKGROUND

The background description includes information that may be useful in understanding the present invention. It is not an admission that any of the information provided herein is prior art or relevant to the presently claimed invention, or that any publication specifically or implicitly referenced is prior art.

Social distancing and the use of personal protective equipment (PPE), such as masks and face shields, have been recommended to protect individuals and control spread of airborne viruses, such as, SARS-CoV-2 (or the COVID-19) virus. However, these measures may not be sufficient to contain the spread of the COVID-19 virus especially in confined spaces. Most face masks have a questionable ability to block fine virus particles. In infected individuals, the masks block the escape of large virus droplets thus forcing them to breathe in more and more viruses with each breath and reinfect themselves with the viruses they should be expelling. Social distancing is of questionable value in a facility where people move around because virus droplets of 10 microns or less in diameter take eight minutes or more to drop from a height of five feet. Inevitably, a "halo" of virus from the infected person lies in wait for the next person to pass by. Lockdowns have only temporary value because the virus is still present in ambient air even after the lockdowns are lifted.

Ideally, the virus must be destroyed or neutered. Recent studies have found that the COVID-19 virus and other variants spread not only through close personal contacts but also over a long distance and for extended periods through the air. Even if the virus droplets fall down within a six-foot radius, the viruses in these droplets are not destroyed. The virus droplets can dry up, releasing virus particles of about 0.1 micron to float into the air converting rooms, buildings, airplanes, etc. These virus-filled confined spaces are analogous to smoke-filled facilities (where the virus is floating around instead of smoke). For example, the COVID-19 virus can infect buildings, airplanes, buses, trains and other structures that have inadequate disinfection functionality in the associated air conditioning system or in air conditioners with sluggish air movement. Such air conditioners can function as a "vector equivalent" for the COVID-19 virus and other microorganisms. Individuals in these confined/enclosed spaces are constantly exposed to this deadly virus every time they inhale the air from such an infected building, structure or conventional mask.

Neither conventional air conditioning systems nor face masks may be able to protect individuals exposed to the virus, because either the masks cannot block such fine virus particles or the masks that can partially block such particles eventually fail due to overloading. The inventor posits that even an N95 mask cannot block these particles completely. Ideally, the air conditioner system can be upgraded to protect against the COVID-19 virus and other microorganisms.

Therefore, there is an ongoing need to provide better systems and devices that are specifically designed to protect an individual or a facility from COVID-19 virus, and other airborne viruses and microorganisms.

SUMMARY

An objective of the present invention is to destroy or neuter COVID-19 virus, and other airborne viruses and microorganisms (collectively known as "virus") outside the human body, to avoid resulting short term and long term complications to the human body. For individual and community protection, and future development of vaccines, the disinfection can be carried out in a graded, predictable and optimal manner, ranging from a total destruction of the virus to just destroying the RNA/DNA component with many variations in between.

In one or more embodiments, the present invention relates to an universal expandable system (or "system") for purification and predictable, graded, optimal, disinfection of air and methods of its use, and in particular to a system and apparatus that eliminates harmful airborne particles and virus from ambient air as it passes through the system, so as to prevent the virus entering the body of a user of the system in the form of a Portable Personal Bio-protection Device (PPBD), or to purify and disinfect an entire air conditioning system by expanding the same unit. In one or more embodiments, the system is configured to protect humans and other mammals from chemical and other contaminations in the air, including poisonous gases, and also to destroy any biological agent that has an ability to cause infection or otherwise damage to human bodies or parts of the human bodies. In an alternate embodiment, the system can also be used to create polyvalent neutered whole virus vaccines and other vaccines where such total protection of the air is not available, affordable, and/or practicable.

The system can include one or more air disinfection sub-systems or modules. In one embodiment, a basic or primary system for neutering whole viruses comprises: (a) an effective first filter to block undesirable particles from the ambient air; (b) a UV-C chamber or filtration unit designed to disinfect the air in a graded predictable and optimal fashion from biological agents like viruses and bacteria; and (c) a second filter to remove poisonous gases, metallic fumes, nuclear fumes, and other noxious fumes. The system can be configured to add one or more additional filtration units and/or UV-C chambers that are designed to address future challenges.

In one embodiment, the resulting neutered whole virus and other pathogens can be used to create polyvalent vaccines. Advantageously, mutated pathogens—which are immune to monovalent vaccines—can also be destroyed using these polyvalent vaccines.

In one embodiment, two filtration units/chambers can be connected to collect a specimen between the two units. The first unit/chamber provides a graded predictable, optimal disinfection. The specimen collected after the first unit can be used to titrate the structure of the neutered/inactivated virus. The second unit is then configured to ensure that no biological agents, including viruses, that might have escaped the first unit are released to the ambient air. The second unit can be configured to substantially destroy all the viruses present within the unit. The information obtained from analyzing the specimens, collected after the first unit and before the second unit, can be utilized for designing products meant for individual protection, building protection, vaccine development, etc. For instance, such information can be used to optimize the size of the PPBD so that the individuals do not have to carry bulky equipment. The information can also be used to optimize vaccine development, sterilize mosquitoes and other pests, by adjusting the degree and strength of the UV-C and the filters in the system.

According to one embodiment, an air disinfection module includes: (a) a UV-C opaque housing having a housing inlet and a housing outlet; and (b) a disinfection chamber having UV-C transparent walls, a centralized inner bore, an interior chamber surface facing the inner bore; a UV-C light source positioned adjacent the interior surface; and a helical air flow diverter centralized within the inner bore proximate to the UV-C light source, wherein the helical airflow diverter creates a helical path for the airflow pathway as the airflow pathway proceeds from the housing inlet to the housing outlet. The helical air flow diverter can be configured as oval if the chamber is oval, and circular if the chamber is circular. The circular air flow diverter in a circular chamber can also be configured such that the circular air flow diverter can turn on its own axis; this will augment the centrifugal redirection of the airflow. In addition, the helical circular air flow diverter can also have obliquely placed septations above and below the helical rungs in their central half to two-thirds of the radius and can further facilitate centrifugal diversion of the air with the particles in the air forced to navigate extremely close to the UV source.

According to another embodiment, an air purification and disinfection system includes: (a) an air mover unit, wherein the air mover controls a rate of air flow through the system; (b) an air disinfection unit having a UV-C opaque housing with a housing inlet and a housing outlet and a disinfection chamber having UV-C transparent walls, a centralized inner bore, an interior chamber surface facing the inner bore; a UV-C light source positioned adjacent the interior surface; and a helical air flow diverter centralized within the inner bore proximate to the UV-C light source, wherein the helical airflow diverter creates a helical path for the airflow pathway as the airflow pathway proceeds from the housing inlet to the housing outlet; and (c) a first replaceable filter having a plurality of septations creating a serpentine airflow pathway going from a filter inlet to a filter exit.

According to yet another embodiment, an air purification and disinfection system includes: (a) a UV-C opaque housing having a housing inlet and a housing outlet; (b) a removable end connected to the housing inlet or the housing outlet; (c) a first replaceable filter having a plurality of septations creating a serpentine airflow pathway going from a filter inlet to a filter exit, wherein the replaceable filter is positioned in the removable end; (d) a plurality of air disinfection units enclosed in the housing, wherein each disinfection unit comprises a UV-C transparent chamber wall, a chamber inlet, a chamber outlet, a centralized inner bore, and an interior chamber surface facing the inner bore; a UV-C light source positioned adjacent the interior surface; and a helical air flow diverter centralized within the inner bore proximate to the UV-C light source, wherein the helical airflow diverter creates a helical path for the airflow pathway as the airflow pathway proceeds from the housing inlet to the housing outlet; and (d) an air mover unit, wherein the air mover controls a rate of air flow through the system.

An adjustable helical air flow diverter found in the disinfection chamber may vary in a variety of ways by: (a) increasing or decreasing in the number of rungs/discs of the diverter for increasing or decreasing the distance of the air flow path and thereby increasing or decreasing the passage time; (b) forcing the air to take a circular path to ensure the resulting centrifugal force will generate a close contact between the pathogens and the UV-C source arranged around the periphery of the chamber; (c) increasing the diameter of the diverter discs, thereby reducing the space between the pathogens and the UV-C sources and chamber walls; (d) making the chamber more lethal to the pathogens by coating the discs and chamber walls with titanium dioxide and/or silver nanoparticles; (e) increasing the reflectivity of the surface of the chambers between the UV-C light sources and the discs to ensure the continuous bombardment of the UV-C energy on the pathogens; (f) making the reflecting surfaces irregular, to increase the UV-C scatter and make the UV-C sources even more effective; (g) arranging the titanium dioxide and the reflecting areas in alternate stripes or superimposing the two; (h) adding protrusions or obliquely placed septations above and below the helical rungs in their central half to two-thirds of the radius to facilitate centrifugal diversion of the pathogen laden air forced to navigate extremely close to the UV-C source; and (i) allowing the helical air diverter to turn on its own axis to augment the centrifugal redirection of the airflow.

According to yet another embodiment, an air purification and disinfection device comprises: (a) a housing having a housing inlet and a housing exit, wherein the housing is opaque to UV-C light; (b) a plurality of disinfection chambers which can be transparent, wherein each disinfection chamber includes a UV source, and a helical air flow diverter; (c) a serpentine air flow path between adjacent disinfection chambers and a helical air flow path within each disinfection chamber; (d) a top lid having a top ballast attached thereto; a bottom lid having a bottom ballast attached thereto; and (e) an inspection window for each disinfection chamber.

The system may also have a conventional HEPA/ultra filter or any other newer or better filters, in a removable entrance unit that takes in the ambient air and runs it through a series of sections in the filter, created by septations, to ensure adequate filtration of such filterable particles. The number of sections and the size of the filters will depend on whether it is for personal use or in conjunction with an air conditioning unit or anything in-between. The air that is filtered through the first filter and disinfected through the UV-C disinfection chamber(s), is then made to pass through another filter, in a removable exit with activated charcoal or any other appropriate agent for the job to filter and destroy poisonous gases, metal fumes, nuclear fumes, and all other harmful, gaseous agents. This filter also has multiple sections designed by septations to ensure prolonged, effective filtration. The arrangement clearly ensures that the air coming out of the unit which the individual breathes, or goes into a building or other confined spaces, through the air conditioners, is totally devoid of viruses and other harmful agents.

On either end of the UV-C chambers, additional chamber units may be added within the housing unit to meet any special requirements. For instance, the smallest unit can have a single chamber and the largest units can have 10-12 (or, theoretically, any number of) chambers that are serially connected by appropriately enlarging the opaque housing unit that holds the UVC chambers. Each chamber has the helical air diverter to force a circular path and create centrifugal force for the air flow. By creating the inlet and the outlet of the chambers at the opposite ends, a lengthy circular air passage is ensured whether it is in one chamber or multiple chambers. The resulting centrifugal force and the double serpiginous passage of air will ensure close contact between the pathogens and the UV-C light for a prolonged and adequate time. The same purpose can be accomplished by connecting one housing to another one each containing one or more UVC chambers (similar to connecting building blocks). This serial connectivity facilitates the creation of a universal, expandable unit.

The duration of contact of the viruses can be increased by increasing the rungs/discs of the helical diverter and the closeness of contact can be increased by reducing the space between the helical diverter and the periphery of the chambers where the UV lights are installed. This universal expandable unit can be used as: a personal unit through a mask or a ventilator through a regular ventilator set up, or a way of purifying and disinfecting the total air conditioning system of buildings, airplanes, buses, trains, boats, ships, etc. by including such units in-line with the air conditioning. This can ensure that no untreated and non-disinfected air can go back to the individual or into the room, airplane cabin, bus, train, ship, or any other confined space.

Depending upon the specific need, the unit can have an AC connection facility or a rechargeable battery provision. The rechargeable battery can also be replaceable. The unit includes an optional pump to control the speed of air passage through the unit. It is especially needed in a personal unit, where the required air flow per minute for breathing should be adjustable. The pump can also work intermittently to coincide with the inspiration of the breath cycle remaining in an off position during the expiration.

Thus, the "expandable" system has the following features: 1) a variable number of septations in the filter and its size to increase efficiency; 2) a variable number of septations in the activated charcoal filter and its size to increase efficiency; 3) provision to increase the number of UV-C chambers from one, to as many as needed; 4) provision to connect one housing unit to more units in series; 5) increase or decrease the number of discs in the helical diverter; 6) increase or decrease the diameter of the helical diverter discs; 7) variation in the overall size of the unit to plan for individual use to the use of a full air conditioning system; and 8) the use of a pump to adjust the air flow speed.

A first and second disinfection housing may be interconnected, where each disinfection housing is constructed similarly. Often the second housing is larger than the first and is meant to accomplish total functional and structural destruction of any pathogens, including viruses, so that the air finally coming out of the second housing will have zero viable, measurable pathogens including viruses. The first unit can be usually variable and is typically used to determine the optimal strength, proximity, and duration of the UV-C to the pathogen to accomplish the desired result. The two unit (or two housing) system is specifically meant to assist creation of graded, predictable and optimal destruction of the pathogen to facilitate creation of polyvalent vaccines, neutered viruses, neutered mosquitos, etc.

The development of polyvalent neutered whole virus vaccine can be explained using SARS-COV-2 as an example. This virus has positive-sense, single strand, RNA combined with nucleoprotein as its core. This type III virus has an envelope made of two main proteins, the M (for membrane or matrix) and E (for envelope) and an "attack" protein projecting out and appropriately called the spike protein. By utilizing two-unit systems, to produce predictable, graded, optimal damage to the virus, it should be possible to produce four types of antigens. The lowest dose of UVC can just neuter the SARS-COV-2 by denaturing the RNA without damaging the architecture of the virus or the four proteins. This product will have four potential antigens from the four preserved proteins for creating a broad-spectrum antibody reaction. By increasing the strength and duration of the UVC and the proximity of the virus to the UVC right inside the first chamber/unit, a second possible product will be a neutered virus with one damaged protein. It will not be difficult to measure the sensitivity of the four proteins to UVC, and by using appropriate dose of UVC the viral antigen can be with four proteins, three proteins, two proteins and just one protein. Since the RNA is denatured in all four of these products, the resulting whole virus cannot multiply in any cell and is not infective. It is difficult to predict which of these four will be the optimal antigen for vaccine. This has to be determined with animal experiments and determination of risks versus benefits. Common sense dictates that the four antigen-antibody vaccine will be the best. In this situation, the virus will have to create mutations against all antibodies at the same time to evade the vaccine. Mutations are "errors" produced during virus multiplications in the cells (accidental evolutionary, random or whatever) but not calculated or intentional. The more viruses in circulation the more chance for mutations. Such mutations take place in each infected person through each virus multiplication cycle. At the peak COVID-19, the estimated number of mutations generated daily in the world was about 100,000 to 1 million.

For any mutation to prevail and propagate, it has to have successful progeny. If mutation does not produce progeny, that particular mutation is usually discarded. In other words, not all mutations result in a new variant.

Reducing the total global circulating virus through PPBD and improvements in air conditioning is the best option to fight SARS-COV-2 infections or other infections, now or in future. Vaccines are the second best option to kill the viruses once they get into the body. The polyvalent vaccine has a better chance to do this. With four types of antibodies to evade, the chances are exponentially lower than with just one type of antibody. The polyvalent vaccine can give a similar challenge to the virus. Partial S protein antibodies are even easier to evade by mutation than total S protein antibodies. If the S protein-lock has seven levers, the mutations have to cover all seven levers. If the antigen is only part of S protein, the antibody produced is only against a few of these seven levers. This makes the mutation much easier.

The present invention is configured to meet the following needs:
(1) Making sure that the user of the present invention only breathes in air that is totally devoid of pathogens. Such a user (including without limitation, an individual human being, other mammal, poultry, etc.) does not breathe in any air directly from the contaminated ambient air. For a healthy individual, the expired air can be released into the air like normal breathing. For an individual with infection in the air passages, the pathogen cannot be released into the air as a way of protecting others. Such expired air can be re-circulated through the unit after taking out the carbon dioxide from the expired air using a soda lime trap or similar unit to absorb the carbon dioxide. Alternately, the expired air can be run through another PPBD to destroy virus and other pathogens, and this disinfected air with the carbon dioxide in it can be released into the air. In this embodiment, there can be two PPBDs, one for inhalation and one for exhalation. Alternately, for an infected individual/patient who is quarantined inside their house, and if there are no other infected individuals in the house, the patient can wear a normal N95 mask with just the PPBD for exhalation to protect other members in the household. There is no need for an inhalation PPBD in this instance. Either of these embodiments can provide greater protection than the infected person wearing a conventional mask and continuing to breathe in their expired air.

(2) Clearing viruses and pathogens in real time, and in a continuous manner through the air conditioning systems of buildings, airplanes, buses, ships, trains and other such confined spaces. Such air conditioners purify and disinfect the air totally before it is released into these confined spaces. The viruses and pathogens released by the individuals, or through the opening of doors and windows are cleared in a continuous manner.

By adapting 1 and 2, the various embodiments of the present invention can prevent any virus from getting through inspired air completely. This can prevent all morbidities that are caused directly or indirectly, in the short term and in the long term, by the airborne viruses and pathogens. Thus, the airborne viruses and pathogens can be killed/eliminated before it enters the body of an individual.

In one or more embodiments of invention, a method for producing polyvalent neutered whole virus vaccine and other similar vaccines through the method of graded inactivation of the pathogens is disclosed herein. Low-cost inhalant vaccines may be the answer to control future pandemics.

Various other objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1A is a perspective view of an air disinfection module according to an embodiment.

FIG. 1B illustrates a sectional side view of the air disinfection module having UV-C light strips.

FIG. 1C illustrates a sectional side view of the air disinfection module having a UV-C tube light.

FIG. 1D illustrates a sectional side view of the air disinfection module having a transparent chamber wall with UV-C light strips.

FIG. 1E illustrates a sectional side view of the air disinfection module with a transparent chamber wall with a UV-C tube light.

FIG. 1F illustrates the air flow path around a helical air flow diverter in the sectional side view of the air disinfection module shown in FIG. 1C.

FIG. 1G illustrates the air flow path around a helical air flow diverter in the sectional side view of the air disinfection module shown in FIG. 1B.

FIG. 1H illustrates the air flow path around a helical air flow diverter as shown in FIG. 1F with coated helical rungs.

FIG. 1I illustrates the air flow path around a helical air flow diverter as shown in FIG. 1G with coated helical rungs.

FIG. 1J is an isometric view of an air purification and disinfection module with its top lid and bottom lid removed, the module having a transparent chamber wall, a UV-C tube light device, a rotation means for the helical air flow diverter, and various coatings on the helical rung surfaces.

FIG. 1K is an isometric view of an air purification and disinfection module with its top lid and bottom lid removed, the module having various coatings on the helical rung surfaces.

FIG. 2 is a perspective view of an air purification and disinfection chamber/device, according to an embodiment.

FIG. 3A is a perspective view of a side section of the air purification and disinfection as shown in FIG. 2.

FIG. 3B is an isometric view of the air purification and disinfection device shown in FIG. 3A with its top lid and bottom lid removed.

FIG. 4 illustrates an air flow pathway through the disinfection chambers of the air purification and disinfection device shown in FIG. 2.

FIGS. 5A-5B illustrate different arrangements of crenulated or irregular surfaces with reflective surfaces and titanium dioxide layers according to an embodiment.

FIGS. 5C-5D illustrate different arrangements of reflective surfaces and titanium dioxide layers on the inner chamber wall according to an embodiment.

FIG. 5E illustrates a combination of reflective surfaces, titanium dioxide, and silver nanoparticle layers on the inner chamber wall according to an embodiment.

FIGS. 5F-5I illustrate how crenulated or irregular surfaces increase the reflections of the UV-C rays from the UV-C source.

FIG. 6A shows an isometric view of the helical air flow diverter with reflective surfaces according to an embodiment.

FIG. 6B shows an isometric view of the helical air flow diverter having a rotation means and protrusions attached to the helical rungs according to an embodiment.

FIG. 6C shows an embodiment of a section of a helical air flow diverter rung coated with reflective materials, silver nanoparticles, and titanium dioxide according to an embodiment.

FIGS. 6D and 6E show the top and bottom of a helical air flow diverter having a rotation means according to an embodiment.

FIG. 6F shows a helical air flow diverter having another embodiment of a rotation means according to an embodiment.

FIG. 7 illustrates an air mover module according to an embodiment.

FIGS. 8A and 8B show filter units having a plurality of septations according to an embodiment.

FIG. 9A shows two interconnected air disinfection modules according to an embodiment.

FIG. 9B illustrates an overview schematic of multiple UV disinfection modules according to an embodiment.

FIGS. 9C-9D show an embodiment of interconnected air disinfection modules within a bellow according to an embodiment.

FIG. 10A illustrates one embodiment of an air disinfection module interconnected with an air mover module according to an embodiment.

FIG. 10B illustrates a sectional side view of the air disinfection device shown in FIG. 10A.

FIG. 11 illustrates the air disinfection module shown in FIG. 1 interconnected with an air mover module and two filter units at opposed ends according to an embodiment.

FIG. 12A shows a perspective view of an embodiment of the air disinfection device shown in FIG. 2 with the top lid removed and with removable entrance and exit ends.

DETAILED DESCRIPTION

Figure 1A:
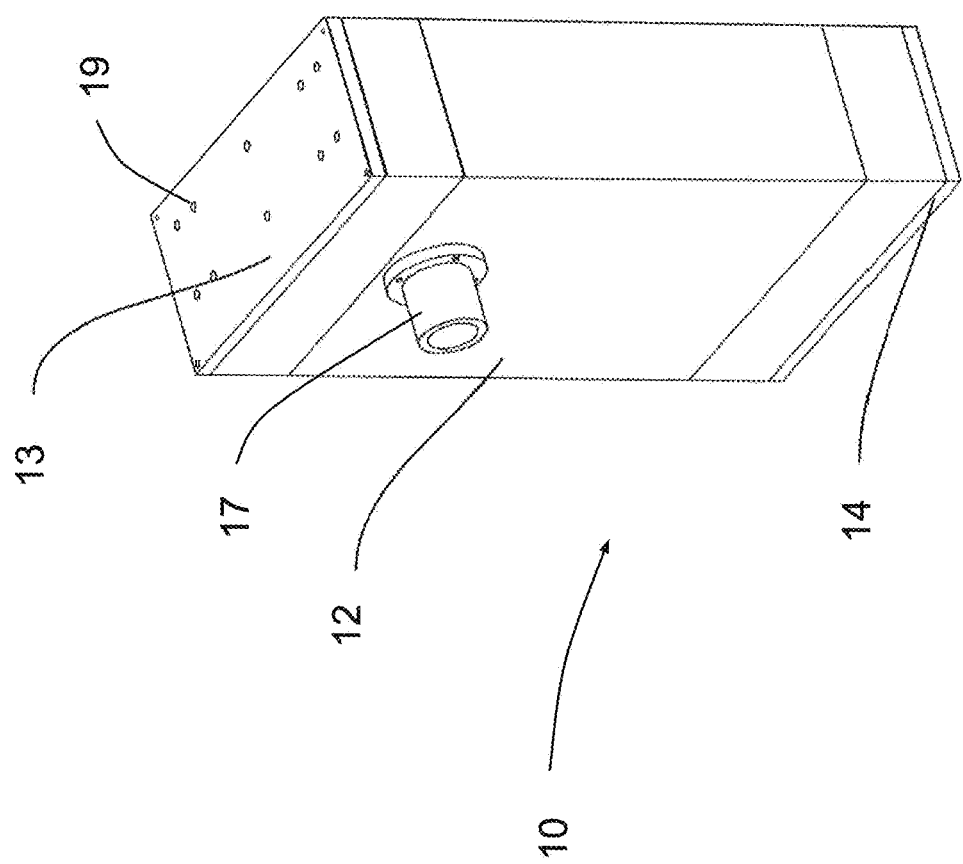

Characteristics and advantages of the present disclosure and additional features and benefits will be readily apparent to those skilled in the art upon consideration of the following detailed description of exemplary embodiments. It should be understood that the description herein, being of example embodiments, is not intended to limit the claims of this patent (or any patent claiming priority hereto). On the contrary, the intention is to cover all modifications, equivalents and alternatives falling within the spirit and scope of this disclosure and the appended claims. Many changes may be made to the particular embodiments and details disclosed herein without departing from such spirit and scope.

As used herein and throughout various portions (and headings) of this patent (including the claims), the terms "invention", "present invention" and variations thereof are not intended to mean every possible embodiment encompassed by this disclosure or any particular claim(s). Thus, the subject matter of each such reference should not be considered as necessary for, or part of, every embodiment hereof, or of any particular claim(s), merely because of such reference. Each of the appended claims defines a separate invention, which for infringement purposes is recognized as including equivalents to the various elements or limitations specified in the claims. Depending on the context, all references below to the "invention" may in some cases refer to certain specific embodiments only. In other cases, it will be recognized that references to the "invention" will refer to subject matter recited in one or more, but not necessarily all, of the claims. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (for instance, "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms are used herein. To the extent a term used in a claim is not defined, it should be given the broadest definition persons in the pertinent art have given that term as reflected in printed publications and issued patents at the time of filing.

The present disclosure relates to a universal expandable system for the purification and disinfection of the air. The system eliminates harmful airborne particles and microorganisms from an airstream as it passes through the system/device before the purified air is delivered to an individual, either directly through a device such as a face mask or after further processing such as through a ventilator, or in larger units, such as, air conditioning units, buildings, airplanes, ships, etc.

One embodiment of a primary/basic system includes: (a) an effective filter to block undesirable particles from the ambient air; (b) one or more UV-C chambers designed to disinfect the air from biological agents like viruses and bacteria; and (c) another filter to remove poisonous gases, metallic fumes, and similar harmful gaseous agents. The system can be used by an individual user or it can be adapted for use for larger structures, such as a room or building. This basic system can be in one air purification and disinfectant device, or it may be made up of multiple modules in various configurations.

Embodiments of the system can include an entire system housed in a single housing; a modular system; or a system having several elements in one housing and additional elements interconnected thereto. Some embodiments of the system include a modular system having one or more modules that can be selectably interconnected to other modules. As used in the description herein and throughout the claims, the term "module" is defined as "each of a set of standardized parts or independent units that can be used to construct a more complex structure".

Typically, the system can be configured for the addition of one or more modules or units, such units may be designed to address multiple challenges including new challenges that arise in the future. The system is versatile to adapt to new technologies and to new or additional harmful airborne particles and microorganisms in order to cover the recipient's needs for purified, decontaminated, and disinfected air. The system can be adapted to the needs of an individual for use through a mask or a ventilator, for a particular room, for a whole building, for airplanes, trains, ships, other public or private transportation units, and any other needs coming up in the future.

Air Disinfection Module

Figure 1C:
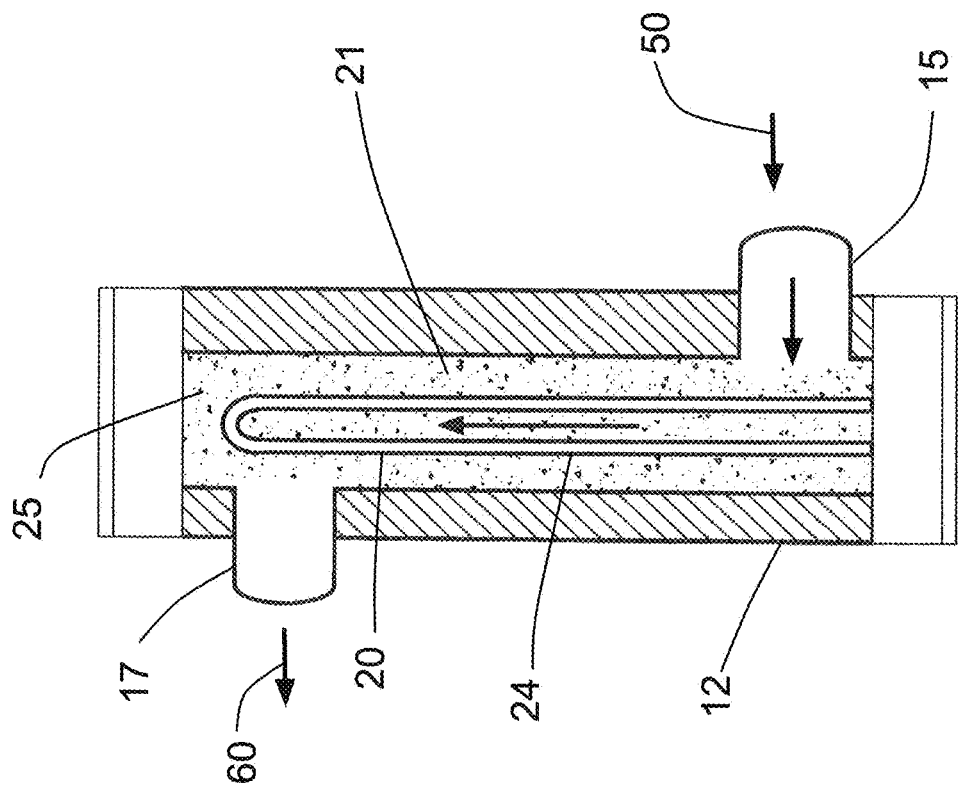
Figure 1B:
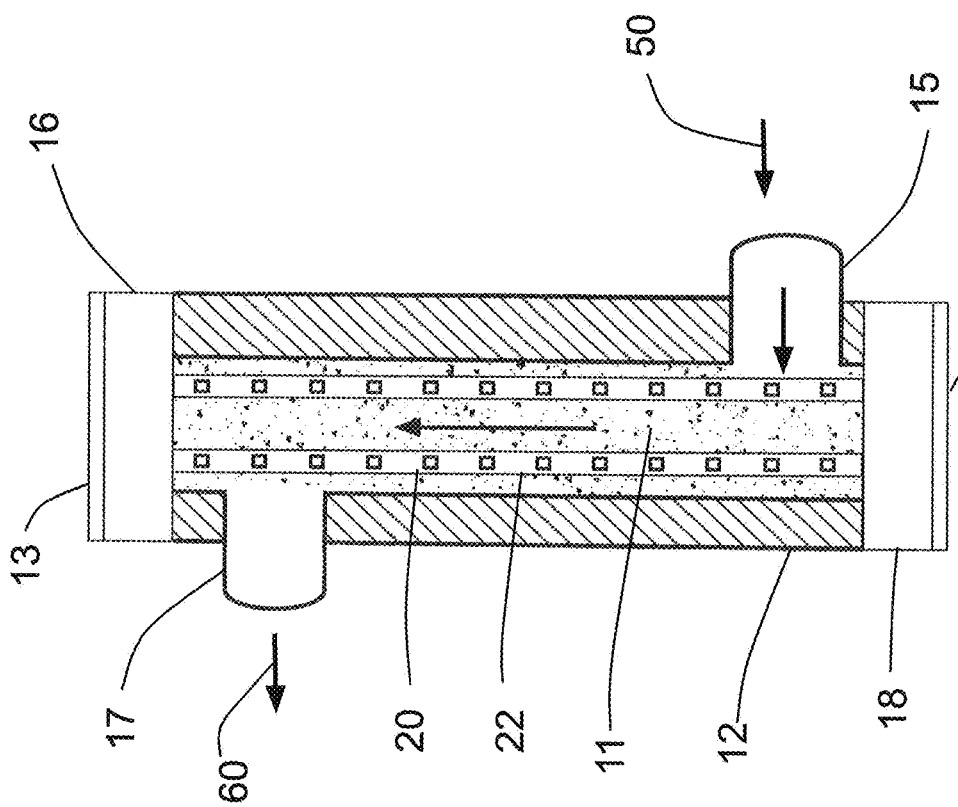
Figure 1E:
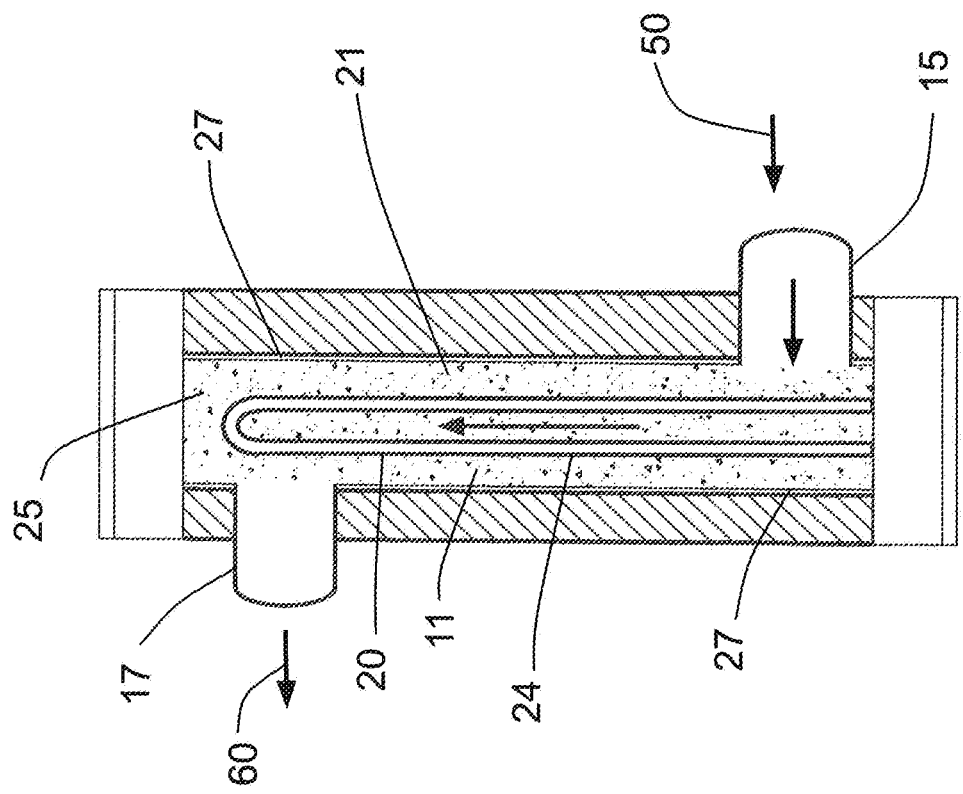
Figure 1D:
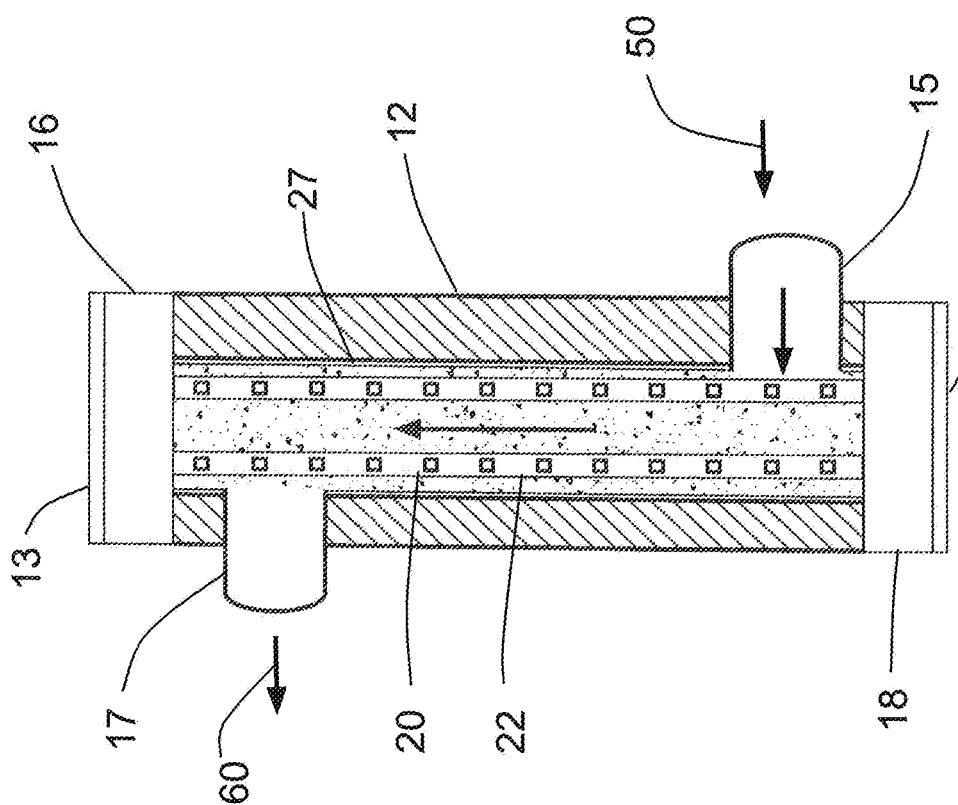
Figure 1K:
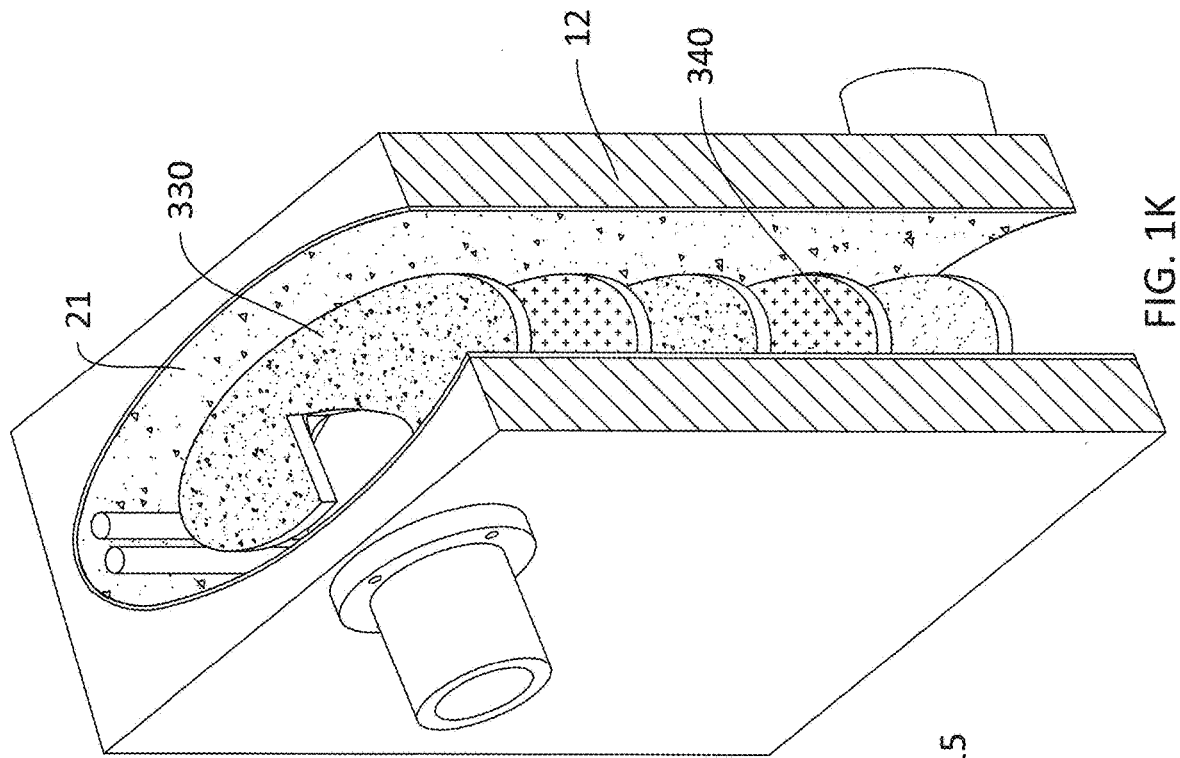

In one embodiment, the universal expandable system for the purification and disinfection of the air has an air disinfection unit/module. One embodiment of an air disinfection module 10 having a single disinfection chamber is illustrated in FIGS. 1A to 1K. FIGS. 1B and 1C illustrate isometric views of the interior of one embodiment of the air disinfection module 10. FIGS. 1D and 1E illustrate isometric views of the interior of another embodiment of the air disinfection module 10. The basic difference in these two embodiments is that the embodiment shown in FIGS. 1B and 1C has a UV opaque chamber wall 12 that also serves as the housing of the device, whereas the embodiments shown in FIGS. 1D and 1E have a UV transparent chamber wall 27 fitted inside the UV opaque housing 12.

The air disinfection module 10 has a single disinfection chamber 11. The disinfection chamber 11 is configured to house at least one UV light source 20 and a helical air flow diverter 30 as shown in FIGS. 1F and 1G. The disinfection chamber 11 houses one UV-C (or UVC) light source 20 or a plurality of UV-C light sources. The disinfection chamber with its UV-C lights 22 and helical airflow diverter 30 irradiates the air flowing through the chamber.

Another embodiment of an air disinfection module 100 has multiple disinfection chambers as illustrated in FIGS. 2, 3A, 3B and 4. The number of disinfection chambers may vary depending on their intended use and the environment that it is designed to be used in.

Housing

FIGS. 1A to 1G show an air disinfection module 10 with a module housing 12 having a housing inlet 15, a housing outlet 17, and a centralized inner bore (or disinfection chamber) with an interior surface 25. The disinfection module, shown in FIGS. 1B and 1C, has a UV opaque chamber wall 12 that also serves as the housing of the device; whereas the embodiment shown in FIGS. 1D and 1E have a UV transparent chamber wall 27 fitted inside its UV opaque housing 12.

The module housing 12 is typically impenetrable by UV light as it is important that the air disinfection device protect the user of the device and the environment around the device from leaked UV light. The module housing has a top lid 13 and a bottom lid 14. The top lid 13 has a number of holes 19 that allow the transfer of heat from one or more heat sinks to the outside air. The top lid also encloses the top ballasts 16. Similarly, the bottom lid 14 encloses the bottom ballasts 18 as also shown in FIG. 1B. The dimensions of the module housing 12 can be varied to ensure the achievement of the disinfection of the airflow traversing the disinfection module 10. The housing 12 may have an optional removable inspection window.

Figure 2:
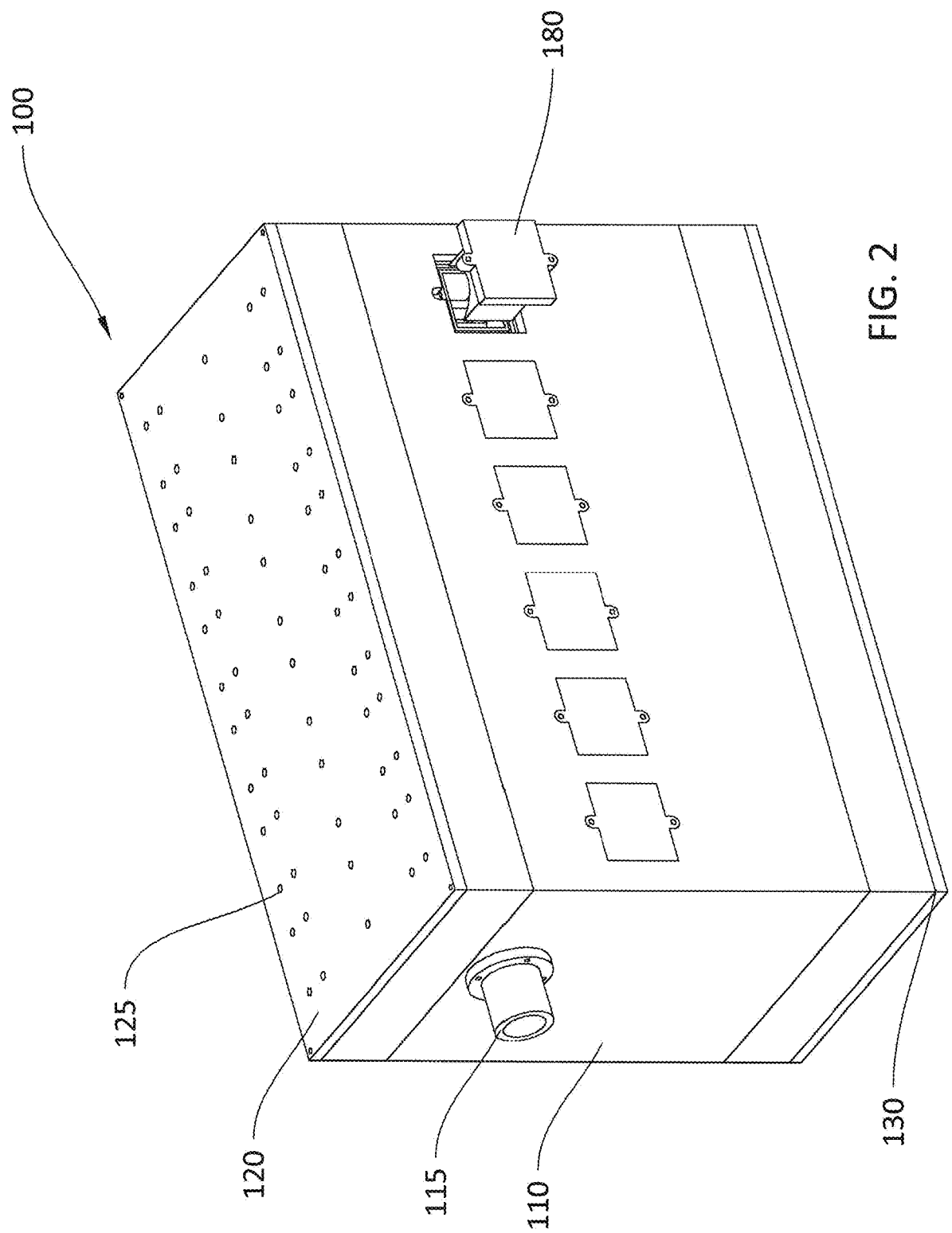
Figure 3A:
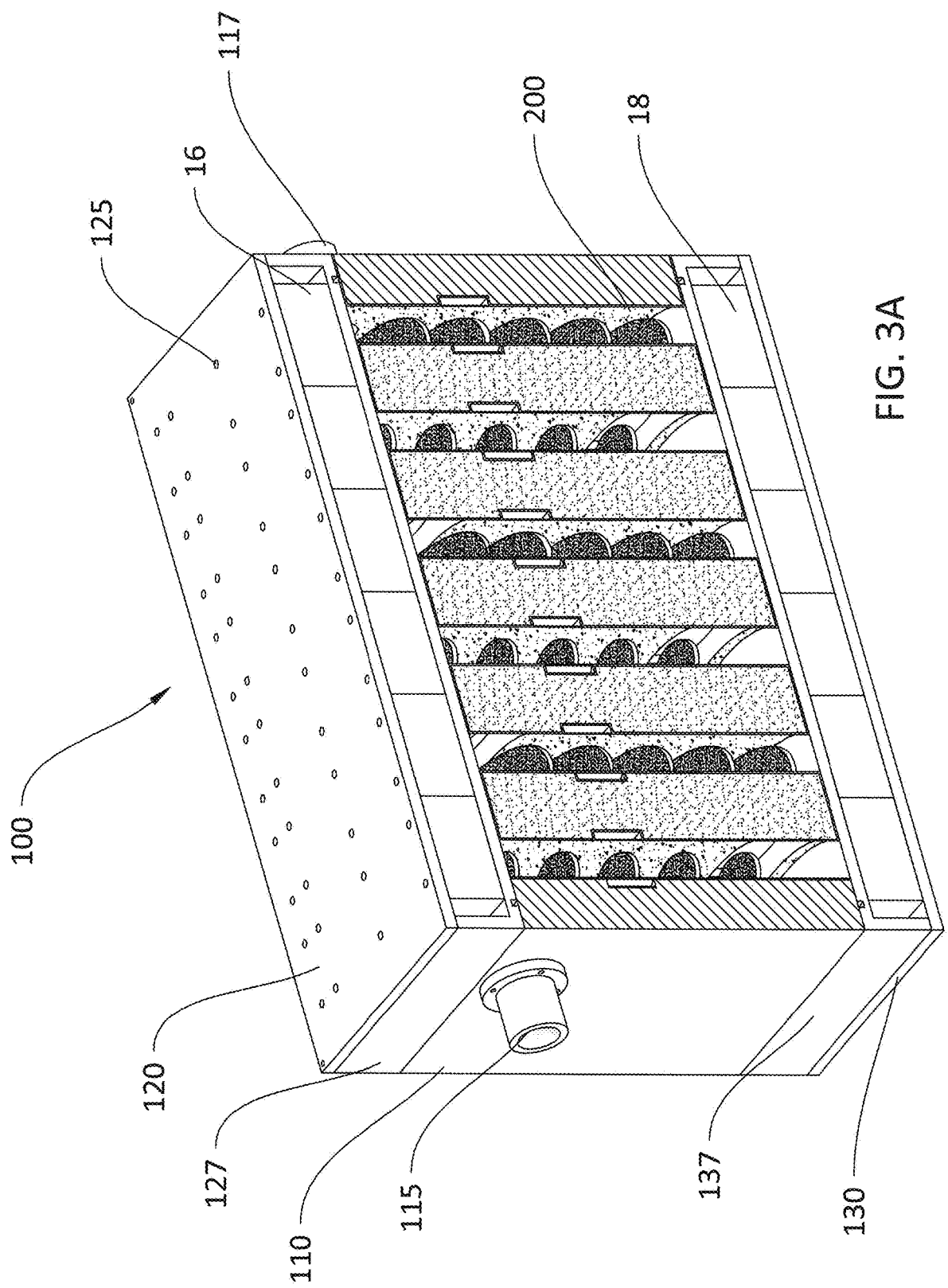
Figure 3B:
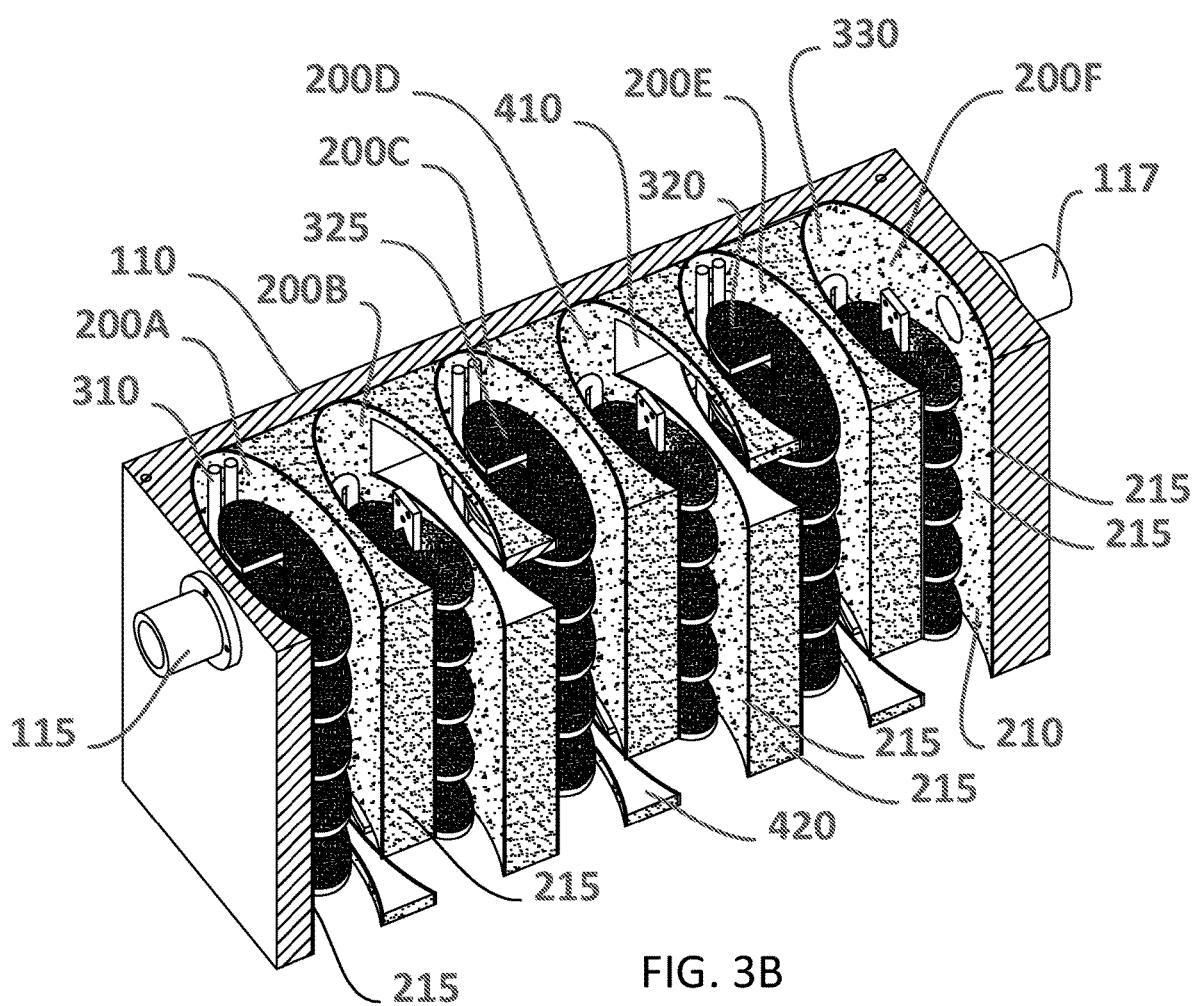

The air disinfection module 100 has a similar housing to disinfection chamber module 10. FIGS. 2 and 3B show the housing 110 with a housing inlet 115 and a housing outlet 117. The housing 110 has a top lid 120 and a bottom lid 130. The top lid 120 has a number of holes 125 that allow the transfer of heat from one or more heat sinks to the outside air. FIG. 3A shows the top lid 120 and a top box 127 enclosing the top ballasts 16 (one for each disinfection chamber) and the bottom lid 130 and a bottom box 137 enclosing the bottom ballasts 18 (one for each disinfection chamber). FIG. 2 also shows an optional removable inspection window 180 for each disinfection chamber 200 of the device. The removable inspection window 180 in each disinfection chamber may be used to monitor the operation and viability of the components of the disinfection chamber as well as allowing an operator of the device to access the interior of the disinfection chamber as needed for maintenance of the internal components of the disinfection chamber 200.

Disinfection Chamber

The air purification modules 10 and 100 have one or more disinfection chambers. Each chamber will have at least one UV-C light and a helical air flow diverter as described in more detail below. FIGS. 1F and 1G are isometric views of the interior of the air purification module 10 and its disinfection chamber 11. The air inlet 15 allows the incoming air 50 to enter the disinfection chamber 11 at one end of the helical air flow diverter 30 and circulate around each rung of the helical air flow diverter 30 until the outgoing disinfected air 60 exits out the air outlet 17.

FIG. 3A illustrates an isometric view of the interior of the air disinfection module 100. The module 100 has a number of disinfection chambers 200 between the inlet 115 and the outlet 117. The disinfection chambers 200A to 200F are separated by UV transparent walls 215 and enclosed in a UV opaque housing 110. Each disinfection chamber 200 is configured to house at least one UV light source 310 and a helical air flow diverter 320 as shown in FIG. 3B. In one embodiment each disinfection chamber houses a plurality of UV-C light sources, such as the UV-C tubes shown in FIG. 3B. Each disinfection chamber with its UV-C lights 310 and helical airflow diverter 320 irradiates the air flowing through the chamber. The air disinfection module 100 may be configured with various different dimensions as selected to fit the needs of the user, including variable heights and widths. For example, an increase in the width of the device allows for the inclusion of more disinfection chambers, whereas an increase in the height of each chamber allows for a longer air disinfection path through each disinfection chamber 200.

Figure 4:
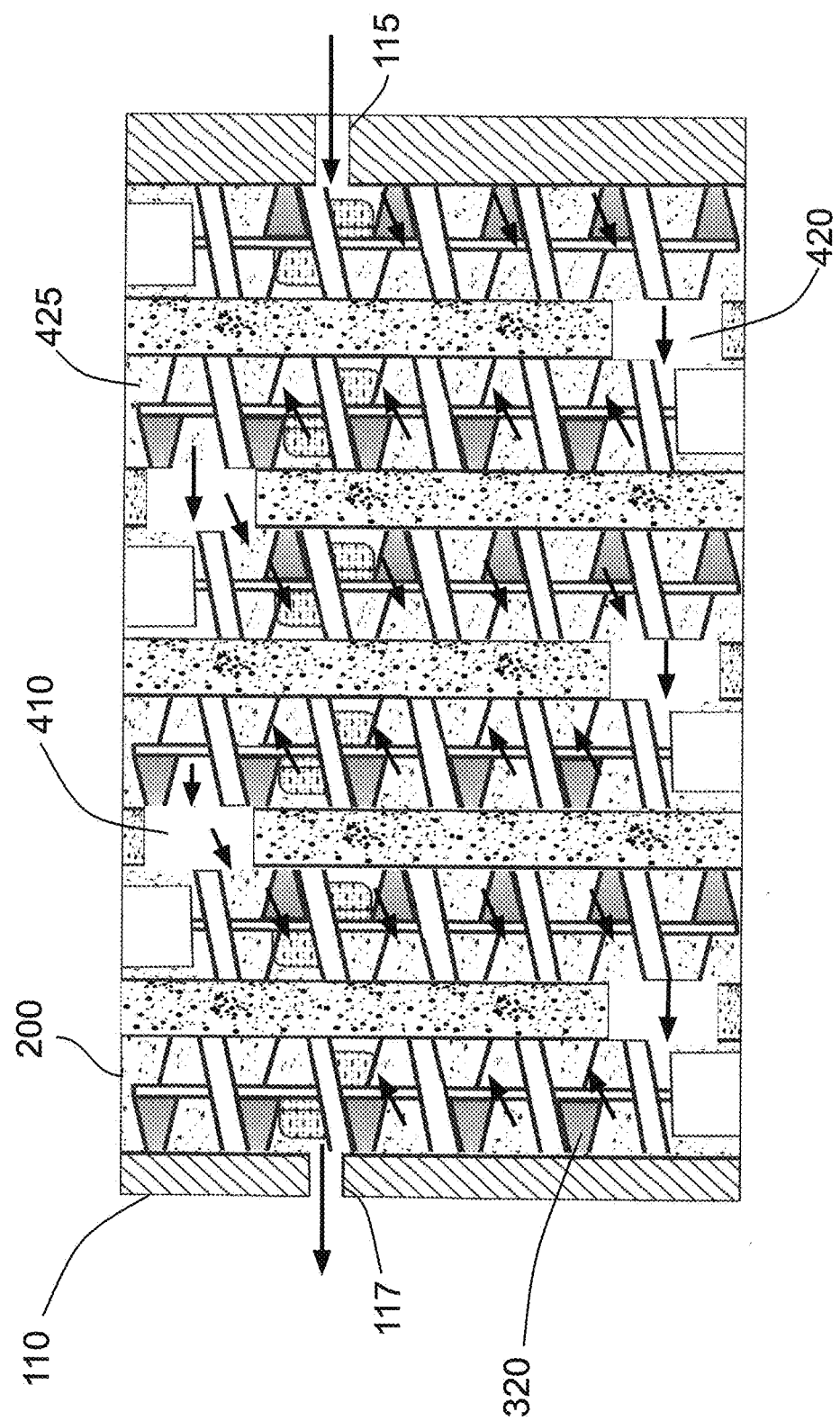

Each disinfection chamber 200 is in fluid communication with its adjacent disinfection chamber(s). As illustrated in FIG. 4, the solid UV transparent walls 215 of adjacent disinfection chambers 200 are connected via alternating upper air passages 410 and lower air passages 420 to create a serpentine air flow path from one disinfection chamber to another disinfection chamber along the length of the device. In addition, the helical air flow diverter 320 provides a helical air flow passage within each of the chambers 200. This serpentine air flow path between adjacent disinfection chambers and the helical air flow path within each disinfection chamber (see FIG. 4) provides increased exposure of the microorganisms in the airflow from the inlet 115 to the outlet 117 to UV-C or far UV-C light emitted by the ultraviolet light sources for an extended and optimal duration, with close contact.

Figure 5G:
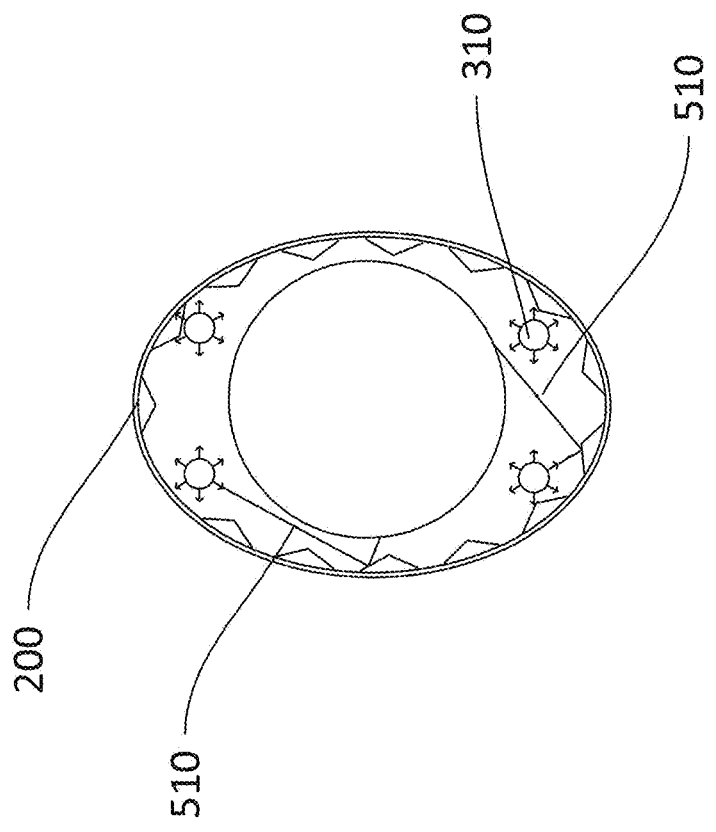
Figure 5F:
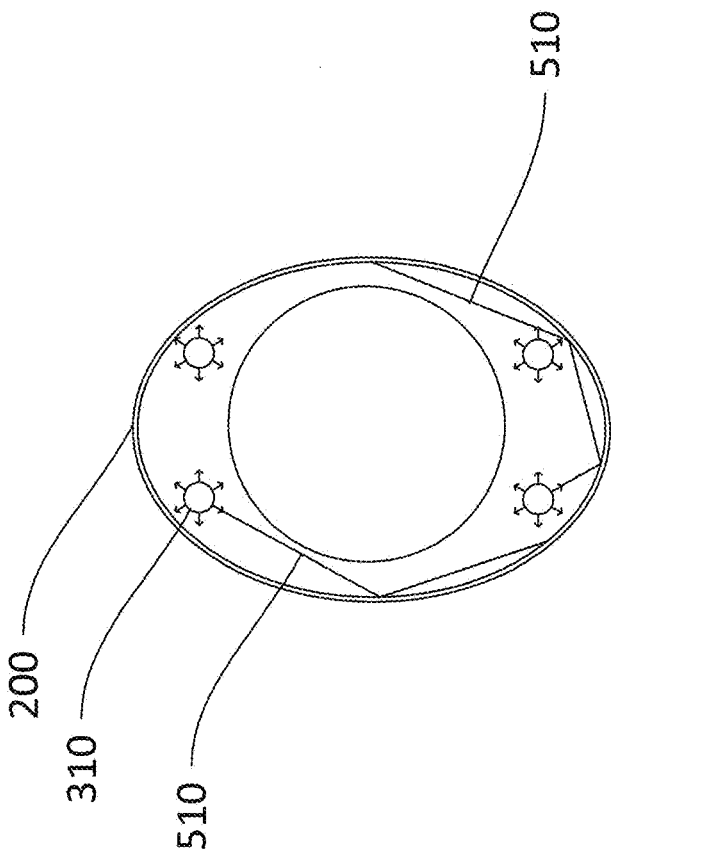
Figure 5I:
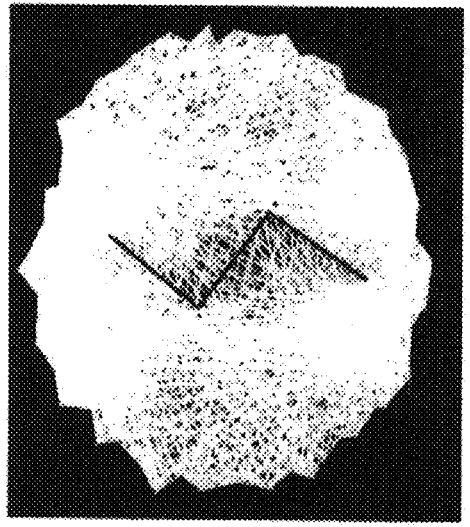
Figure 5H:
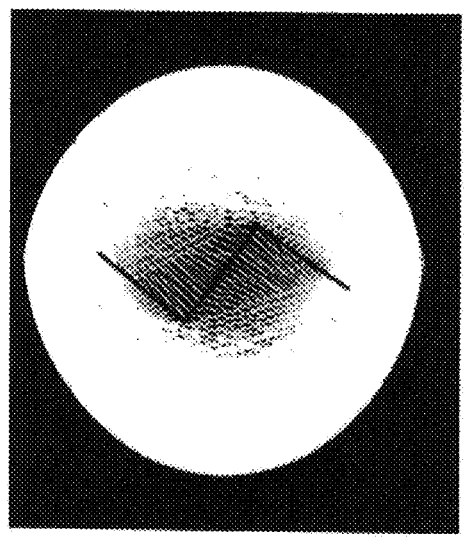

To further increase the effectiveness of the disinfection chamber 11 or 200, the internal chamber surfaces 25 or 210 respectively may be optionally lined with reflective material, silver nanoparticles, and/or titanium dioxide to concentrate the UV-C and also to make the device more lethal to the microorganisms in the air flow. As illustrated in FIGS. 5C, 5D and 5E, the reflective, titanium dioxide coatings, and silver nanoparticle coatings can be coated, layered one over the other, or they can be in alternate up and down longitudinal strips inside the chambers.

In addition, as shown in FIGS. 5A-5B and FIGS. 5E-5I, the surface of these reflecting, titanium dioxide coated, and/or silver nanoparticle coated walls, can be made irregular or crenulated to increase the light ray reflections. The multiple reflections of the UV-C will impinge the microorganisms on all sides, and the titanium dioxide can augment the lethality of the disinfection chamber towards all microorganisms. FIGS. 3B and 4 illustrate that the incorporation of reflecting, titanium dioxide, or silver nanoparticle coated walls 425 and/or irregular or crenulated areas in the interior disinfection chamber wall 210 can be used to increase the light ray reflections.

As previously discussed, the air flow path and therefore the time and exposure of the air flow to the UV-C sources 310 within the air disinfection module may be adjusted by (1) adjusting the number of disinfection chambers 200 in the device, (2) adjusting the height of the disinfection chamber and thus the height of the helical air flow diverter, (3) adjusting the number of helical rungs in the helical air flow diverters, (4) varying the surface on the interior wall of the disinfection chamber with reflecting, titanium dioxide coating, silver nanoparticle coated walls and/or irregular or crenulated walls to increase the light ray reflections; and/or (4) adjusting the speed of the air flow through the device.

UV Light Source

UV light is a well-known disinfectant. Many UV light emitting devices are available in the marketplace. These devices are used to "sterilize" surgical suites, airports, and other such spaces. However, for effective disinfection, the UV light has to be strong enough to destroy the microorganisms within a close proximity. Additionally, the microorganisms have to be exposed to the UV light for a sufficient duration of time before they are neutralized. Such high energy UV radiation and long exposure to UV radiation can injure normal human cells like skin, cornea, and other cells. Therefore, UV light should not be allowed to come near the hands or other area of the skin. Furthermore, exposure of the skin to UV radiation can cause skin irritation and other ailments.

UV light is an electromagnetic radiation beyond the wavelength of the visible violet or beyond the spectrum that the human eye can see. The UV light itself has a spectrum ranging from 100 nanometers to 400 nanometers. UV light having wavelengths from 315 nm to 400 nm is called UV-A, from 280 nm to 315 nm is called UV-B, and from 200 nm to 280 nm is called UV-C. Far UV-C light has a spectrum ranging from 207 nm-222 nm. For the purposes of this application, the terms "UV-C" and "far UV-C" are used interchangeably.

The earth's ozone layer blocks the UV-C but allows UV-A and UV-B to reach earth. The shorter the light wavelength is, the less it will penetrate human skin. UV-A and UV-B can damage human skin and are the ones implicated in sunburn, skin cancer, and an increased risk of cataracts. UV-C from the sunlight cannot normally reach the earth because it is filtered out by the earth's ozone layer. Far UV-C and UV-C light penetration into the skin is low but is sufficient to cause some damage. However, UV-C light penetrates microorganisms and denatures their RNA and/or their DNA, causing cell damage and making the reproduction of those microorganisms impossible.

The kill rate of UV-C light depends on the specific microorganism you are trying to destroy as well as the UV-C dosage the organism receives. Dosage (J/m2) is a combination of exposure time and intensity (microwatts per square centimeter). UV_dose=UV_bulb_power*Exposure_time/(4*pi*UV_bulb_distance^2. The intensity is a measure of the power of the UV-C and its proximity to the organism, where Intensity, E=UV_bulb_power/UV_bulb_distance^2.

The number, type, and the placement of the UV-C lights 20 in the disinfection chamber 10 will ensure that the bacteria and viruses in the air flow passing through the disinfection chamber 10 will receive a sufficient UV-C dosage to kill any microorganisms in the air. Likewise, the number, type, and the placement of the UV-C lights 310 in each disinfection chamber 21 will ensure that the bacteria and viruses in the air flow passing through the disinfection chamber 200 will receive a sufficient UV-C dosage to disinfect the air flowing through the device.

The UV-C light source 20 or 310 can be any type of UV-C light source, such as the UV-C tubes 24 shown in FIG. 1C or the UV-C light strips shown in FIG. 1B. UV-C light sources may include mercury lamps, fluorescent tubes, pulsed xenon lamps, excimer lamps, UV-C LEDs, and UV-C lasers. Once the UV-C light source is selected and the wattage or irradiance is known, the exposure time to achieve the desired dosage can be calculated and the appropriate time for the air path to spend passing through the disinfection chambers in close proximity to the UV-C lights can be determined. In fact, when more than one disinfection chamber is used, different UV-C light sources may be used in the different chambers. Different UV light sources may be selected for the different wavelengths that they produce, their different intensities, their different lifespans, the difference in their heat production, or for any other reason.

Helical Air Flow Diverter

One embodiment of the helical air flow diverter 30 is illustrated in FIG. 1F. The helical air flow diverter provides a helical air flow passage within the disinfection chamber 21. Typically, the helical air flow diverter fills most of the empty space in the disinfection chamber as seen in FIGS. 1F through 1I thereby creating an air flow path that circulates around each helical rung in a narrow space between the disinfection chamber wall 25 and the helical air flow diverter rungs 315. Thus, as the air flows from the inlet 15 to the outlet 17, it circulates close to the UV-C light source(s) throughout the disinfection chamber(s).

Figure 6A:
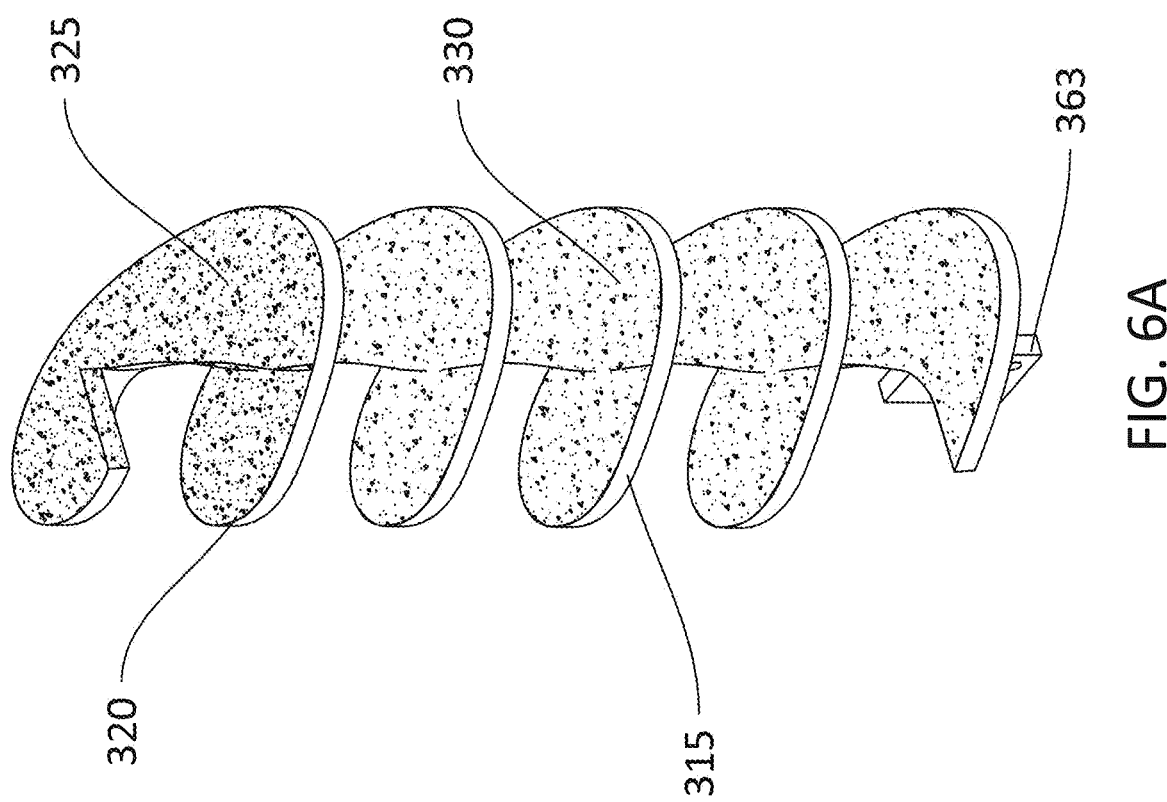

A similar embodiment of the helical air flow diverter 320 is shown in FIG. 6A. It has most of the same characteristics as the helical air flow diverter 30 but has its surface 325 coated with reflective materials 330. The helical air flow diverter surface 325 may be optionally lined with reflective material 330, titanium dioxide 340, and/or silver nanoparticles 350 with or without areas of irregular or crenulated surfaces as shown in FIGS. 1J, 1K, 6B, and 6C. The embodiment of the helical air flow diverter shown in 6B has a vertical axis with a rounded top 365 and/or bottom 370.

Figure 1J:
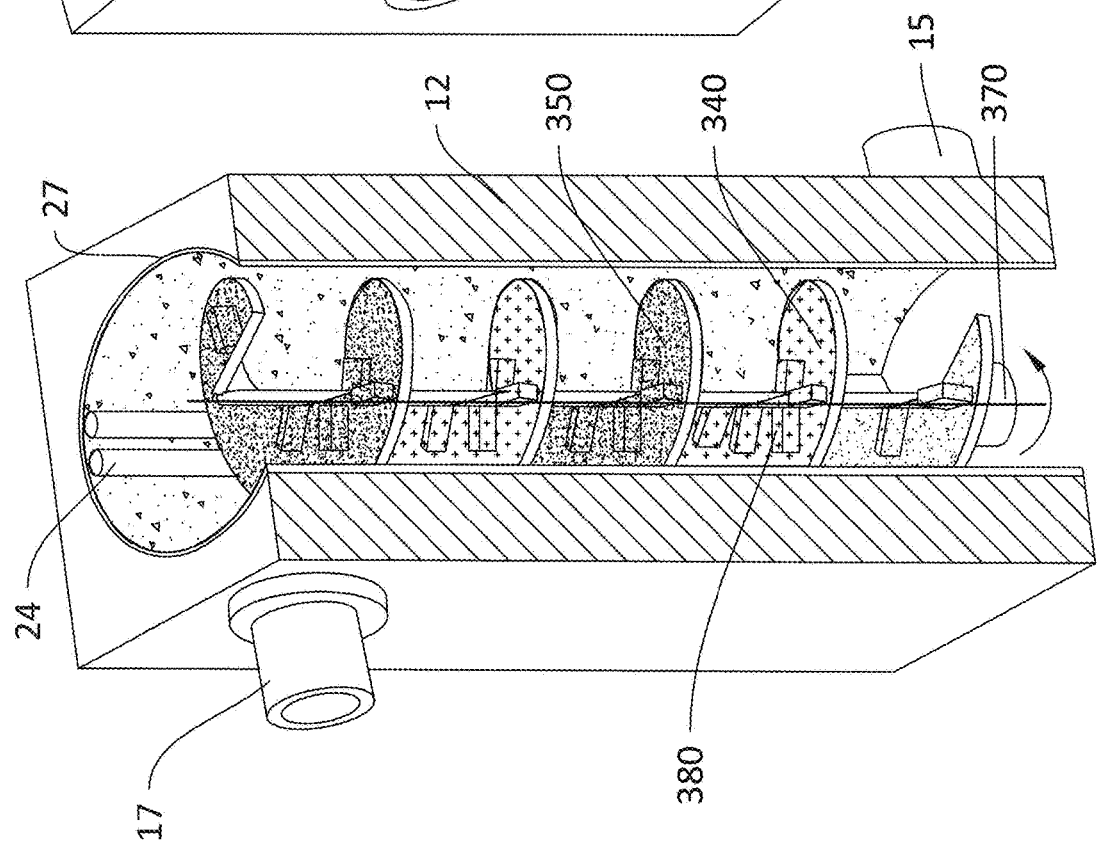
Figure 14:
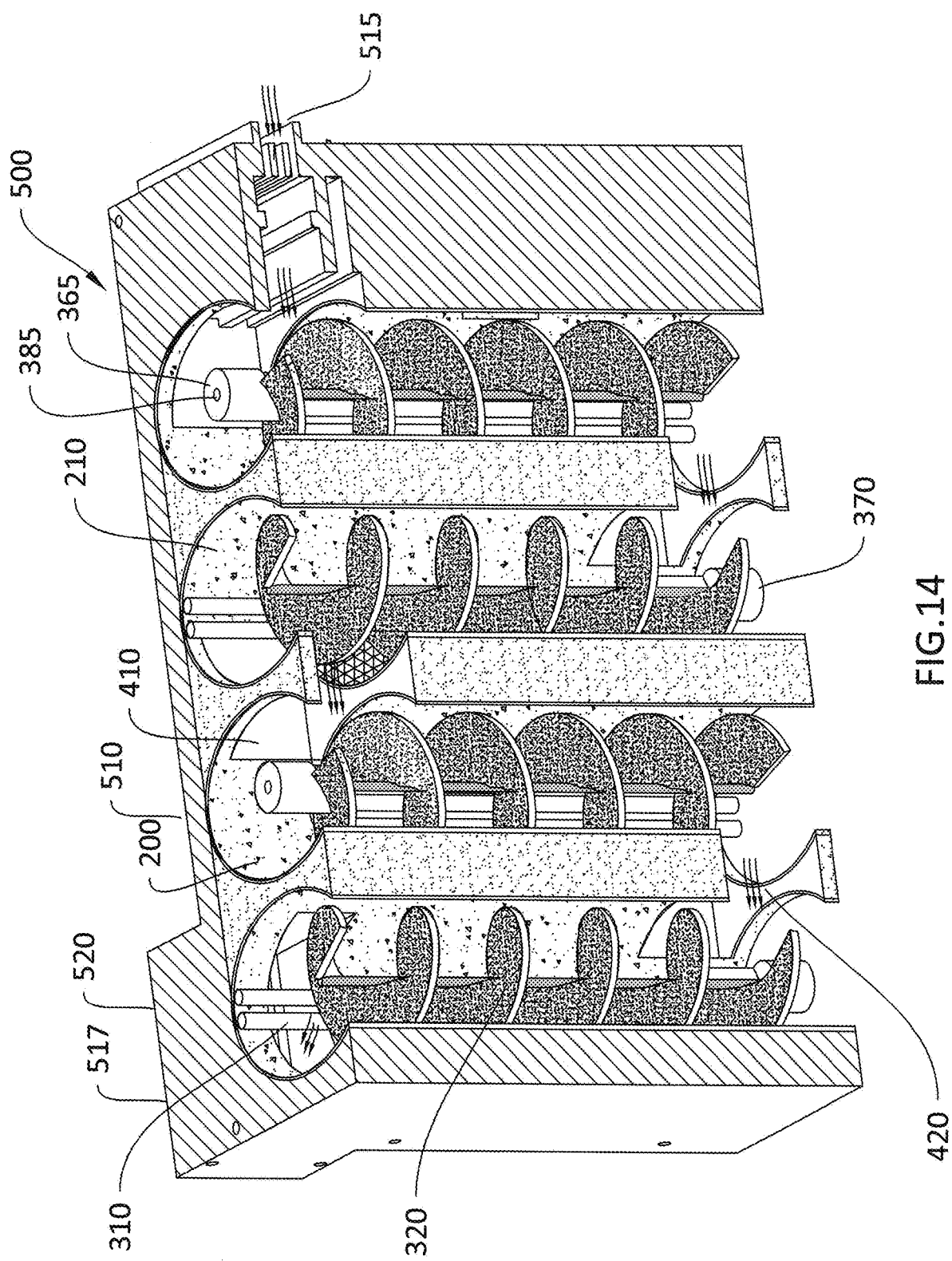
FIG. 14 illustrates side perspective view of an air purification and disinfection device showing the interior of its disinfection chambers within a housing with an extended outlet end according to an embodiment.

Some embodiments of the helical diverter 30 and 320 are fixed within the disinfection chamber via a post 363, a rectangular example of the post is shown in FIG. 6A. Other embodiments of the helical inverter include a rotational means that allows the helical diverter to rotate within the disinfection chamber. Embodiments of the rotational means include allowing the helical diverter to rotate about a rounded bottom 370 as illustrated in FIGS. 1J and 6B or allowing the helical diverter to rotate about a rounded top 365 and bottom 370 fitted into rounded indentations in the top box 127 and in the bottom box 137 respectively, thereby providing another rotational means for the helical air flow diverter 30 or 320 as illustrated in FIGS. 6D and 6E. Yet another embodiment of a rotational means is shown in FIG. 14, wherein the helical air flow diverter 320 is shown with an aperture 385 or bore through a tubular core 380 along its vertical axis that can freely rotate about pins at the top and bottom of the disinfection chamber.

Furthermore, the embodiment of the helical air flow diverter shown in 6B has a number of protrusions along the rung 315 surfaces. One embodiment of these protrusions are oblique septations on the top and bottom of the helical rungs 315, preferably within about one-half to two-thirds of the radius of the rung. The septations will further facilitate centrifugal diversion of the pathogen-laden air to navigate the air stream extremely close to the UV-C source.

The adjustable helical air diverter found in the disinfection chamber may have at least three variables for: (a) variations in the number of rungs/discs 315 of the diverter, where increases in the number of rungs will further interrupt a direct air flow path and increase the passage time; (b) variations in the air speed in a circular path around the rungs of the air diverter to vary the centrifugal force on the air to provide a closer contact between the pathogens and the UV-C source arranged around the periphery of the chambers; (c) increasing the diameter of the diverter discs, thereby reducing the space between the pathogens and the UV-C sources and the chamber walls; (d) making the chamber more lethal to the pathogens by coating the discs with titanium dioxide, silver nanoparticles, and/or increasing the reflectivity of the surface of the chambers between the UV-C light sources to ensure the continuous bombardment of the UV-C energy on the pathogens as illustrated in FIGS. 5A through 5E; and (e) making the reflecting surfaces irregular or crenulated 335 to increase the UV-C scatter and make the UV-C sources even more effective as shown in FIGS. 5A and 5B.

The air disinfection module 100 has multiple interconnected disinfection chambers 200 as seen in FIG. 3A. In a similar manner as in the air disinfection module 10, the helical air flow diverter 320 (see FIG. 6) in each of the disinfection chambers 200 provides a helical air flow passage within each disinfection chamber as shown in FIG. 4. Interlinking the disinfection chambers 200 to create a serpentine air flow path between adjacent disinfection chambers in addition to the helical air flow path within each disinfection chamber 200 (see FIG. 4) provides increased exposure of the microorganisms in the airflow from the inlet 115 to the outlet 117 to UV-C or far UV-C light emitted by the ultraviolet light sources 310 for an extended and optimal duration, with close contact. The air flow path and therefore the time and exposure of the air flow to the UV-C sources 310 within the device may be adjusted by (1) adjusting the number of disinfection chambers 200 in the device, (2) adjusting the height of the disinfection chamber and thus the height of the helical air flow diverter, (3) adjusting the number of helical rungs in helical air flow diverters, and/or (4) adjusting the speed of the air flow through the device.

Variations Within the Disinfection Chamber

The air disinfection module 100 may be configured with a wide variety of different dimensions as selected to fit the needs of the user, including variable heights and widths. For example, an increase in the width of the device allows for the inclusion of more disinfection chambers, whereas an increase in height of each chamber allows for a longer air disinfection path through each disinfection chamber 200. In one embodiment the disinfection chambers may be configured to be selectably connectable to other disinfection chambers.

Examples of other variations include: varying the strength of the UV-C sources, varying the proximity of the microorganisms in the air flow to the UV-C sources, varying the distance travelled by the air stream, and varying the time and proximity that the air steam is exposed to the UV-C light sources in the disinfection chambers 200 within air disinfection module 100.

Figure 6F:
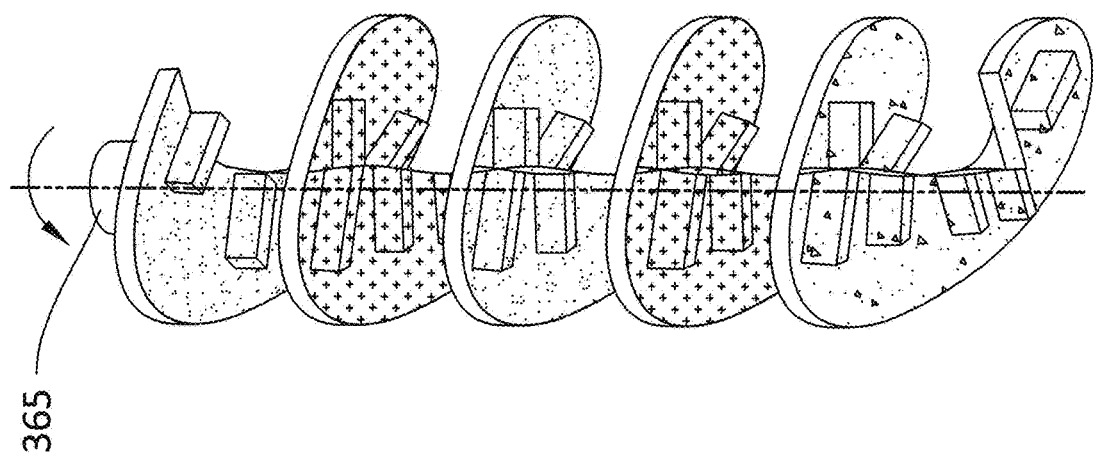

To further increase the effectiveness of the disinfection chambers 200, the internal chamber surfaces 210 and/or the helical air flow diverter 320 and/or their surfaces 325 are optionally lined with reflective material and/or titanium dioxide as discussed above. Likewise, the helical air flow diverter surface 325 may be optionally lined with reflective material and titanium dioxide with or without areas of irregular or crenulated surfaces as shown in FIG. 6.

The helical air diverter found in the disinfection chamber may have one or more variables for: (a) increasing or decreasing in the number of rungs/discs of the diverter for breaking down the air flow and increasing the passage time; (b) forcing the air to take a circular path to ensure the resulting centrifugal force will generate a close contact between the pathogens and the UV-C source arranged around the periphery of the chambers; (c) increasing the diameter of the diverter discs, thereby reducing the space between the pathogens and the UV-C sources and chamber walls; (d) making the chamber more lethal to the pathogens by coating the discs with titanium dioxide or silver nanoparticles and/or increasing the reflectivity of the surface of the chambers between the UV-C light sources to ensure the continuous bombardment of the UV-C energy on the pathogens; (e) making the reflecting surfaces irregular, to increase the UV-C scatter and make the UV-C sources even more effective; (f) adding protrusions or obliquely placed septations above and below the helical rungs; and (g) allowing the helical air diverter to turn of its own axis to augment the centrifugal redirection of the airflow.

Air Mover

The air purification and disinfection system of the present invention relies on the air source to travel through the air purification module to disinfect and neuter the microorganisms in the air. The air purification and disinfection system may utilize an air mover or air circulator, such as an air pump or a fan, in communication with the air purification module inlet or outlet to ensure a controlled rate of air flow through the air purification module. The helical air path through each disinfection chamber will extend the time that the air is exposed to the UV-C light sources. The time the air spends in the disinfection chambers is further controlled by the speed of air movement through the chambers as controlled by the air mover. The speed of air movement through the system may be adjusted by adjusting the power level going to the air mover.

Figure 7:
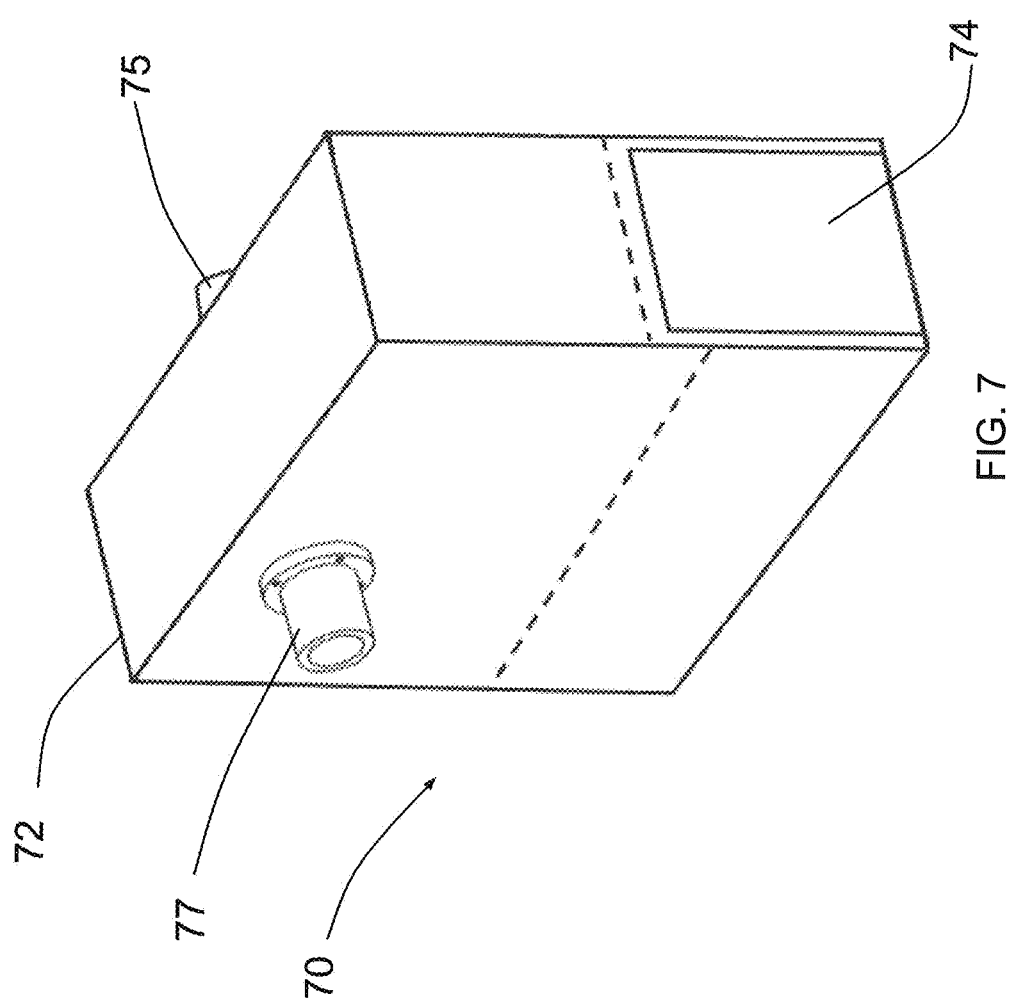

An air mover module 70 may be a standalone module, as illustrated in FIG. 7, or it may be interconnected to one or more modules in the air purification and disinfection system via tubing or any other means. The air mover module 70 has an inlet 75, an outlet 77, an air mover 72 (such as a pump or fans), and a power pack 74 (such as a battery).

The air mover controls the movement of the air through all of the modules of the entire system such as (a) air disinfection module(s), filtration module(s), etc. The air mover functions at different power levels that can be electronically controlled. By altering the power level of the air mover, the air circulation can be made faster or slower.

Air Purifier

Figure 8A:
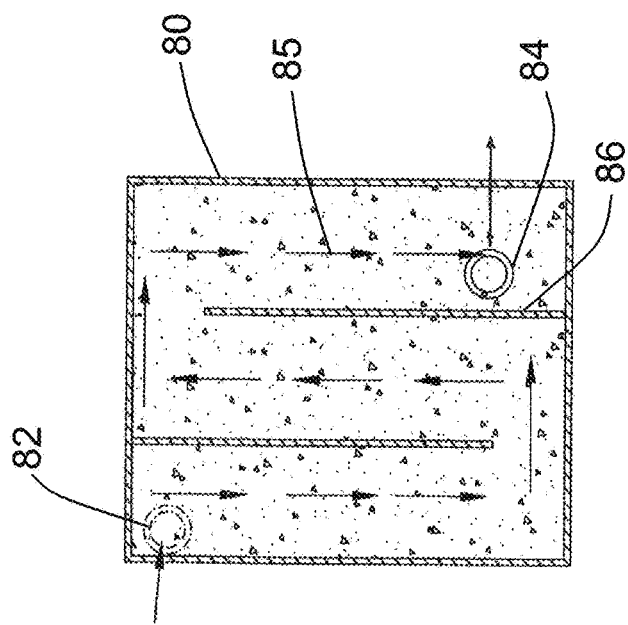

The air purification and disinfection system may include one or more replaceable air purifiers that remove unwanted substances from the air flow through the system. Some embodiments of the system include one or more air purifiers. The air purifiers may be incorporated into the system as individual modules or incorporated into one or more of the air disinfection modules One type of air purifiers are filters. Several embodiments of the system include one or more individual filter modules. For example, airflow entering the system may be filtered to filter out fine particulates and/or microorganisms. Exemplary filters are High Efficiency Particulate Air filters (i.e., HEPA filters) or 0.22 micron filters. One embodiment of a HEPA filter 80 is shown in FIG. 8A. The HEPA filter has an air inlet 82 so that the incoming air flow (e.g., ambient air, recirculated air, or some other processed air stream) enters one end of the HEPA filter. Once it enters the HEPA filter, the air path 85 flows throughout the HEPA filter in a serpentine fashion around a number of partitions 86 and exits an outlet

84. This serpentine filtration path increases the efficiency of the filtration process. The filtration process can be further enhanced by increasing the size of the HEPA filter 80, increasing the partitions 86 or septations, and/or varying the air speed through the filter.

A carbon dioxide absorption filter may be included in some systems. One embodiment of the carbon dioxide absorption filter is a replaceable canister having a material that can absorb carbon dioxide from an incoming airflow. The material can include, without limitation, soda lime, Baralyme™, or Amsorb®. The air passing through a carbon dioxide absorption unit will be substantially free of carbon dioxide.

Humanity is slowly moving away from natural products to synthetic materials. Pesticides are examples of this "evolution." While creating a better standard of life, the industrial revolution also brought in the inevitable lowering of air quality. Neither the industrial revolution, nor its inevitable air contamination has seen the end yet. This means that the air quality will continue to deteriorate. By incorporating a second filter designed to remove poisonous gases, metallic fumes, and similar harmful gaseous agents the system can address future air quality challenges by removing such undesirable elements like pesticides, metallic fumes, and even nuclear waste materials. For example, an activated charcoal filter may be used to absorb and remove any heavy metal fumes, volatile organic compounds, or other toxic/poisonous vapors that may be in the air supply or generated within the disinfection chamber.

Figure 8B:
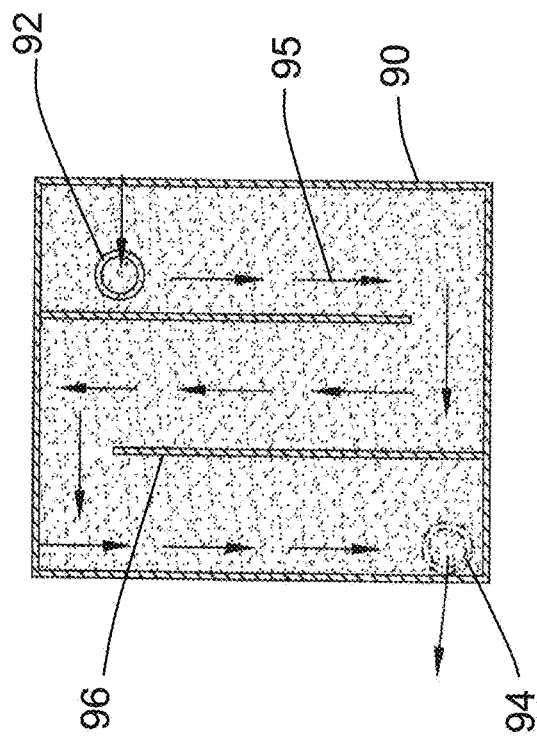

One embodiment of an activated charcoal filter 90 is shown in FIG. 8B. The activated charcoal filter has an air inlet 92 so that the incoming air flow (e.g., ambient air, recirculated air, or some other processed air stream) enters one end of the activated charcoal filter. Once it enters the activated charcoal filter, the air path 95 flows throughout the activated charcoal filter 90 in a serpentine fashion around a number of partitions 96. This serpentine filtration path increases the efficiency of the filtration process. The filtration process can be further enhanced by increasing the size of the activated charcoal filter 90, increasing the number of partitions 96 or septations, and/or varying the air speed through the filter. The activated charcoal filter 90 also has an air outlet 94 to allow the disinfected air to flow out of the activated charcoal filter 90.

Exemplary Interconnected Modules

The modules used to create specifically designed air purification and disinfection systems can be interconnected in numerous ways. The modules can be simply connected via hoses between the inlets and outlets of different modules. This type of connection can be used to curve or bend around corners. Other embodiments of the modules may be snapped or clasped together in innumerable ways, or several modules may be enclosed within a single housing or box.

Figure 9A:
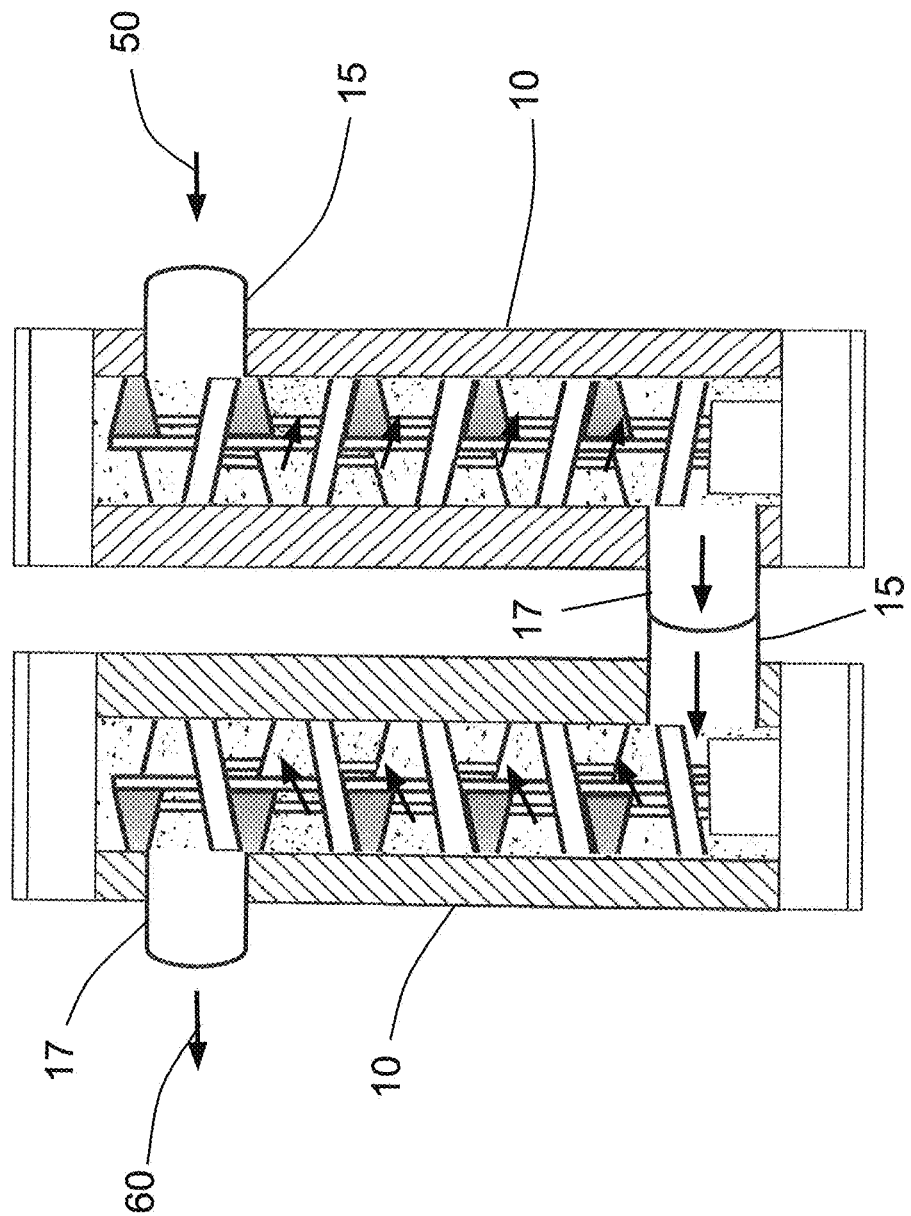

FIG. 9A shows two interconnected air disinfection modules. For example, one embodiment, shown in FIG. 9A, has an air disinfection module 10 connected to another air disinfection module 10. In this embodiment, the incoming air 50 enters the air inlet 15 of a first disinfection chamber, circulates through the first disinfection, and then the first disinfected air stream enters a second disinfection chamber to be further disinfected before it exits the outlet 17 of the second disinfection chamber.

Figure 9B:
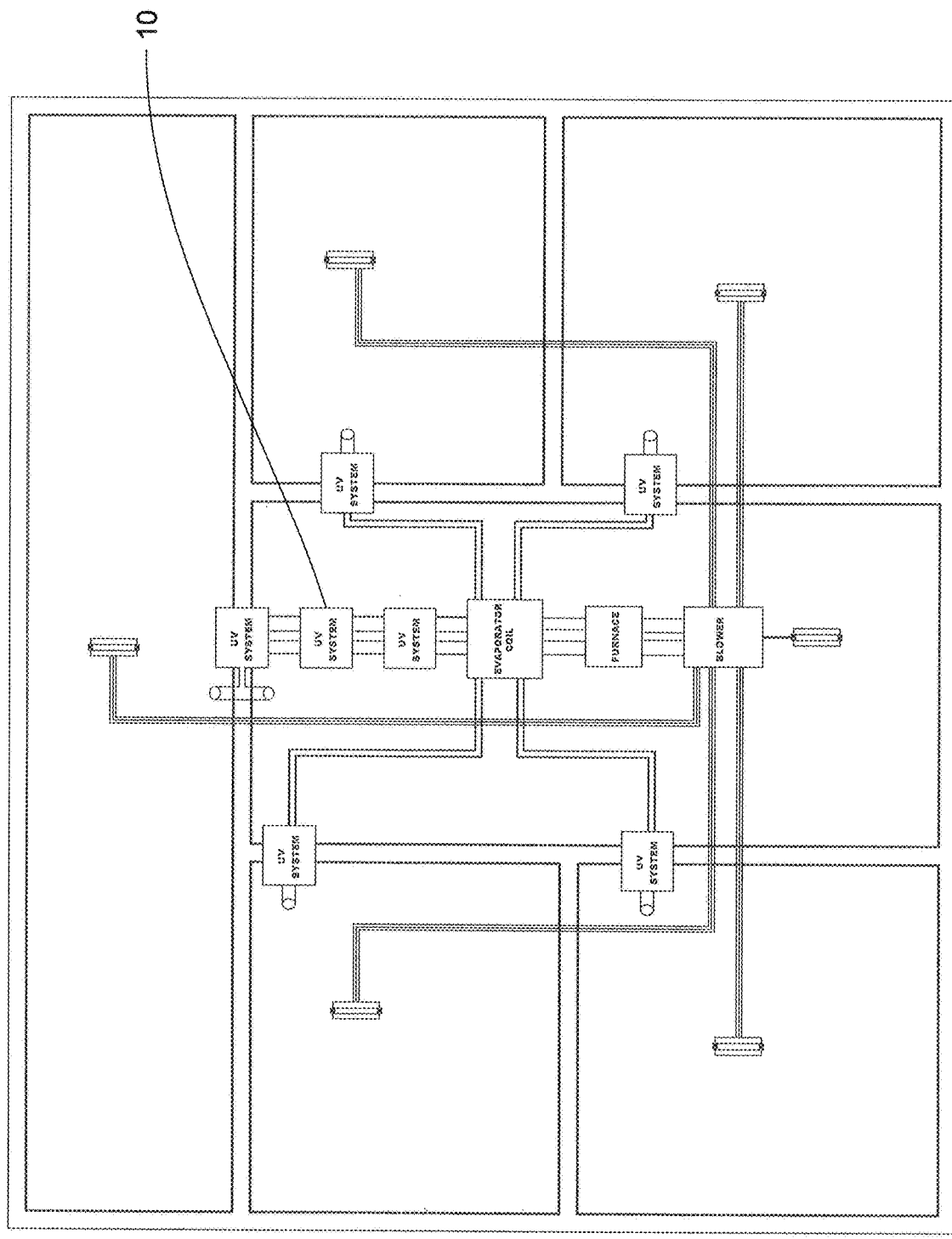

FIG. 9B illustrates an overview schematic of multiple UV disinfection modules 10 incorporated into a building, for example in an attic. The network of multiple UV disinfection modules 10 can be used to provide the UV disinfected air into multiple rooms or sections of buildings. For example, bigger areas like waiting areas or corridors can have multiple modules 10 interconnected as a single expandable system, whereas the smaller rooms can have individual independent modules 10, as described herein.

Figure 9C:
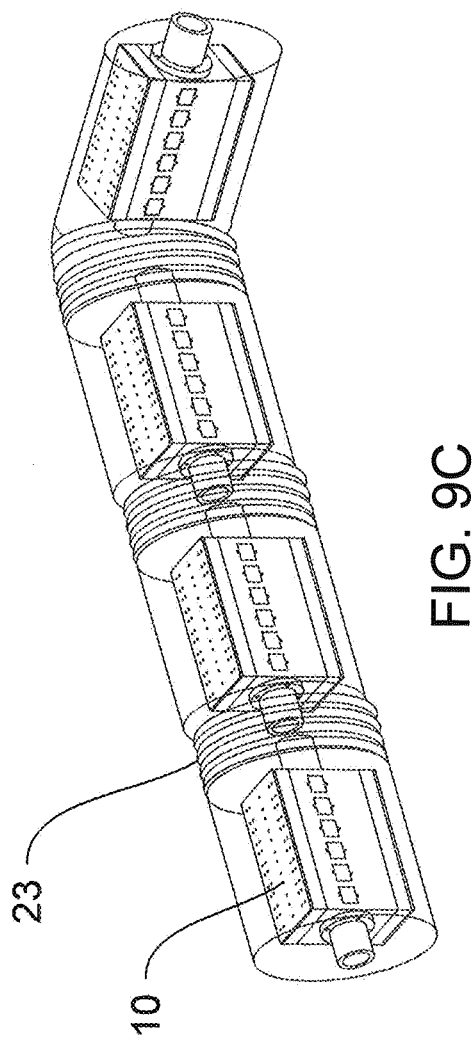

FIG. 9C depicts an embodiment of an expandable disinfection system for a building located, for example, in an attic. The disinfection system can be expanded by increasing the number of UV disinfection modules 10. Additionally, the expandable disinfection system expands by adding a plurality of modules 10 with connection each module. The connection may be in the form of bellows 23, so that the air from one module does not go out into the ambient air but is forced to go into the next module.

Figure 9D:
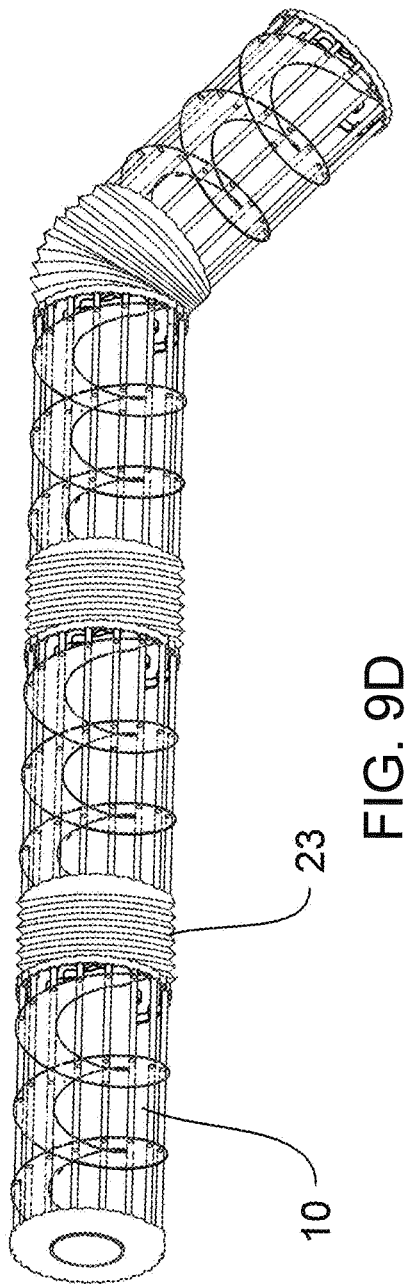

FIG. 9D illustrates another embodiment of an expandable disinfection system for a building. Similarly, to FIG. 9C the UV disinfection modules 10 are within the bellows 23. Additionally, as shown in FIG. 9D, the modules may be a different UV disinfection arrangement, for example, utilizing the individual cylindrical modules as described in reference to FIG. 6A.

Figure 10A:
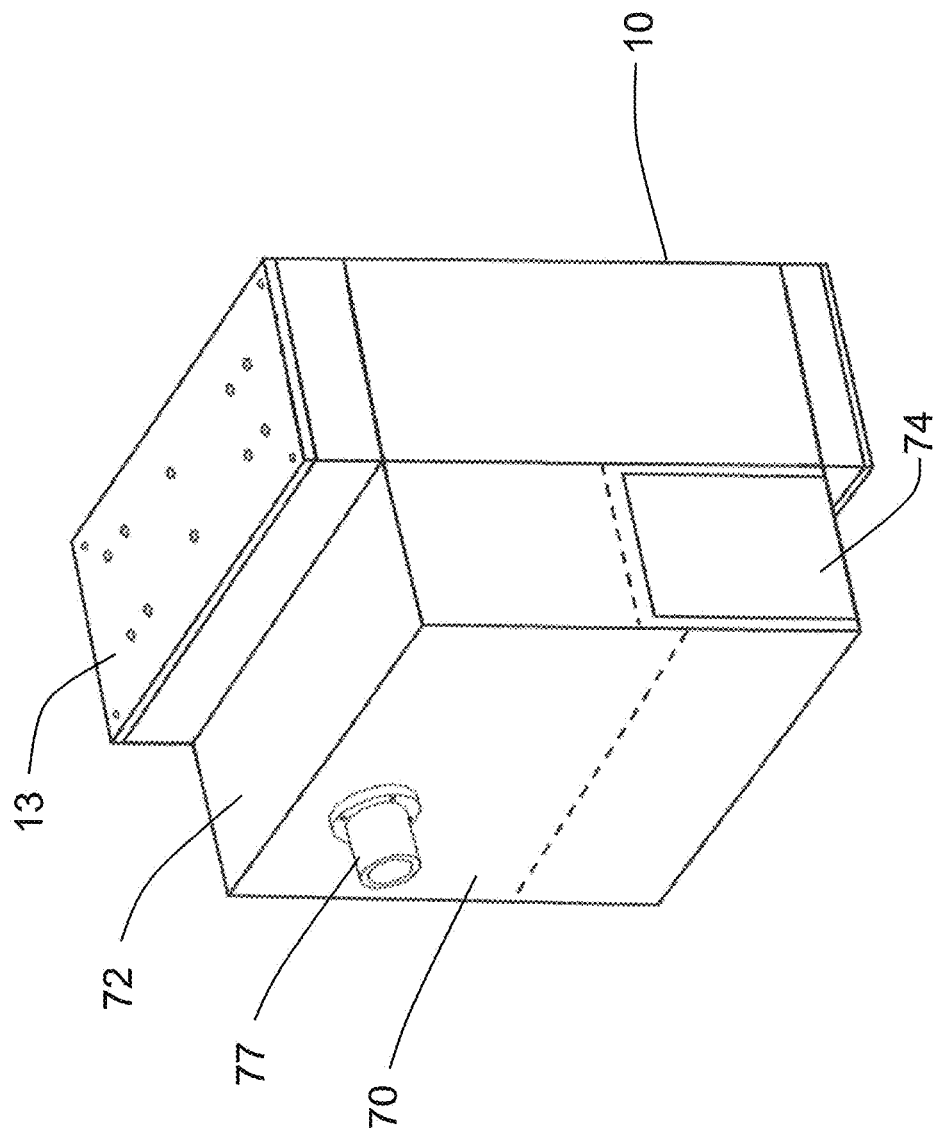
Figure 10B:
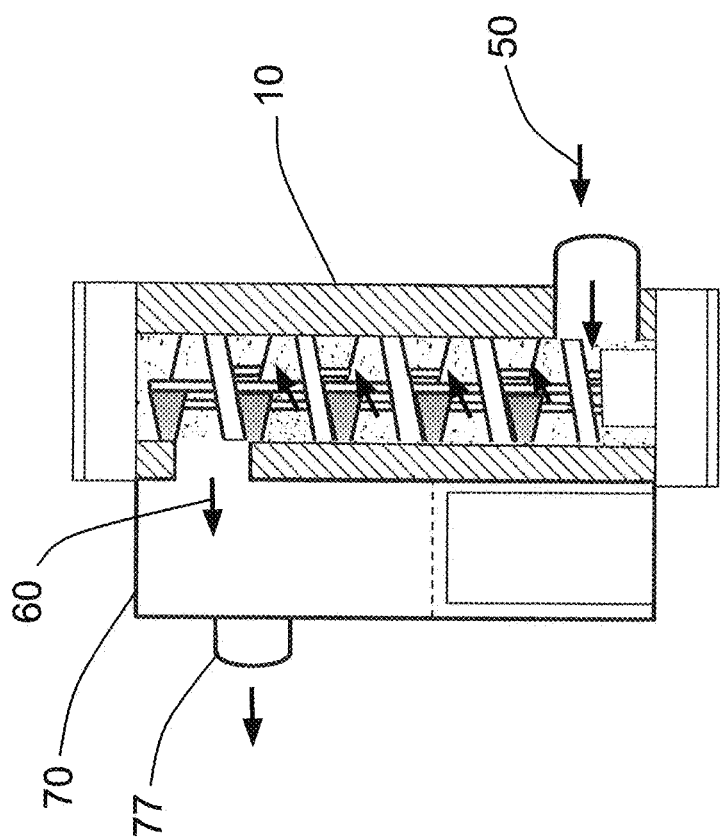

Another embodiment, shown in FIGS. 10A and 10B, has an air disinfection module 10 connected to an air mover module 70. The incoming air 50 circulates through the disinfection chamber 10. The air stream is disinfected in the disinfection module 10 and the disinfected air stream 60 enters the air mover module 70. The air speed or velocity of the air stream through the system is governed by the air mover or pump.

Figure 11:
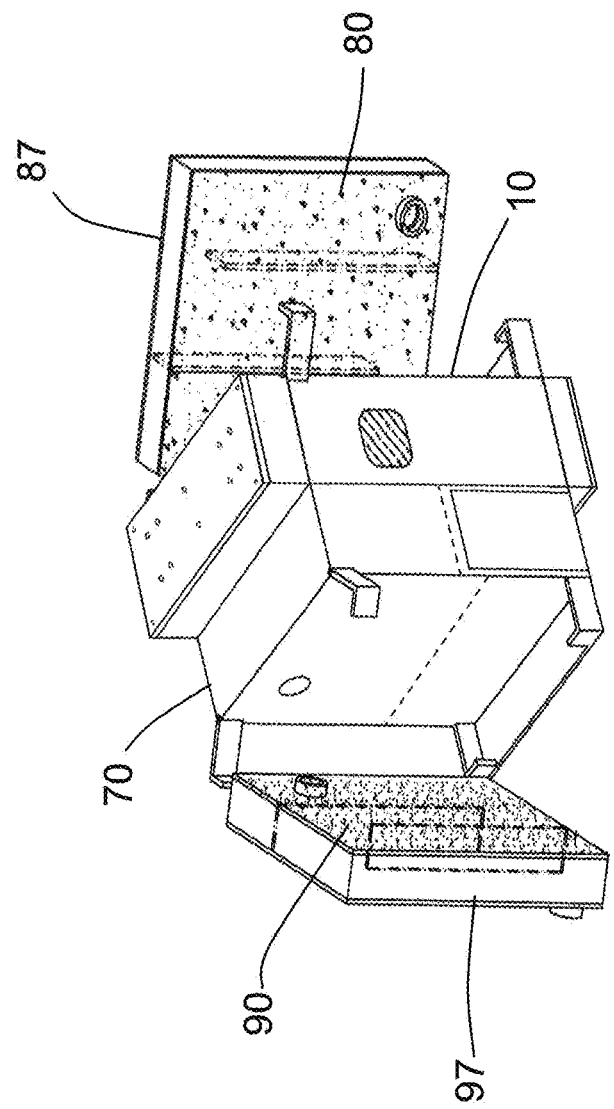

The embodiment shown in FIG. 11 interconnects a disinfection module 10 and an air mover module 70 similar to those shown in FIG. 10A. However, the embodiment shown in FIG. 11 also includes a replaceable HEPA filter 80 and an activated carbon filter 90. The disinfection chamber 10 has an attachment means wherein an entrance door 87 containing the HEPA filter 80 can be clamped onto the air inlet side of the disinfection chamber. The air mover module 70 has a similar attachment means for clamping an exit door 97 containing the activated carbon filter 90 onto the air outlet side of the air mover module.

Figure 12A:
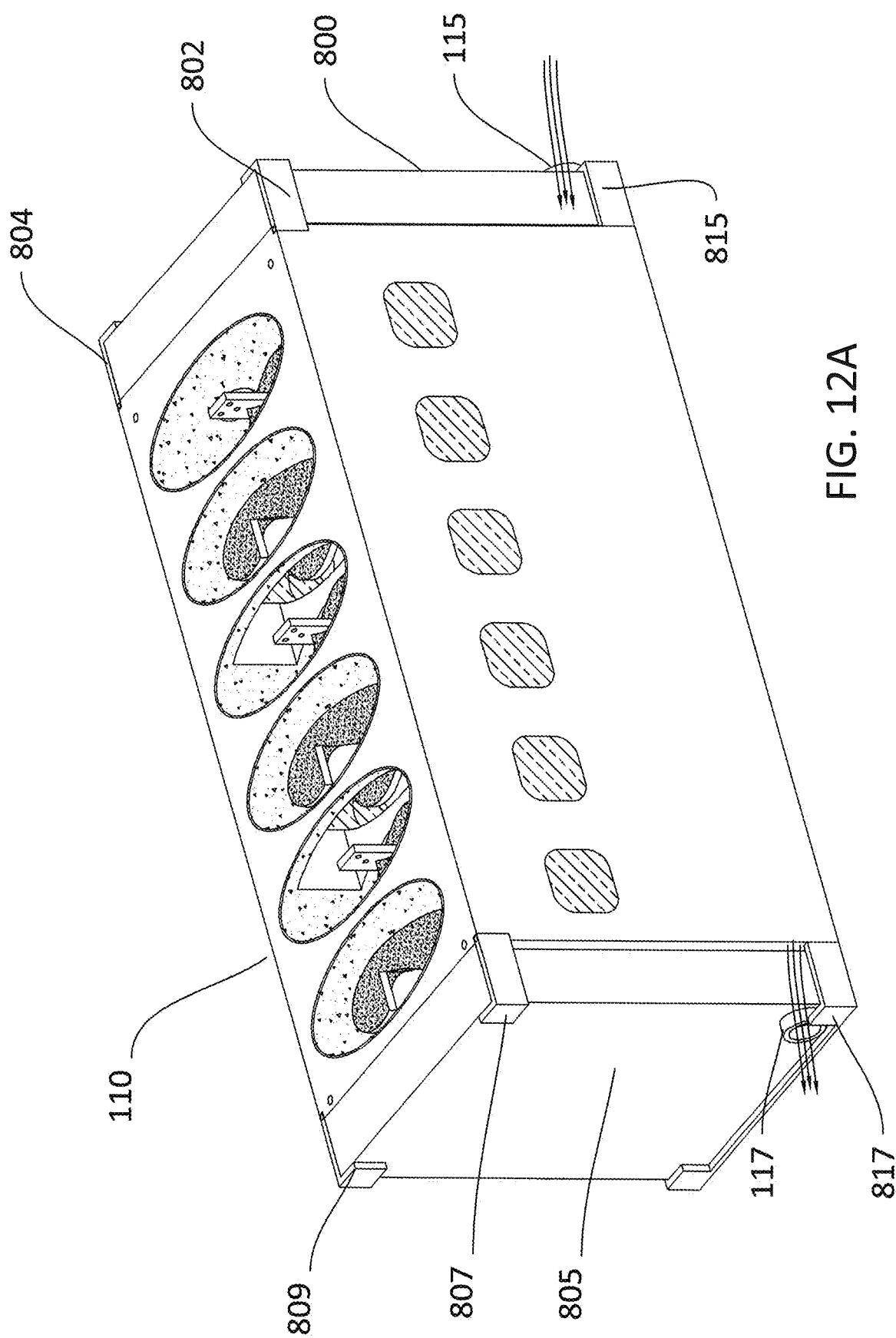
FIG. 12B shows the air purification and disinfection device shown in FIG. 12A with the entrance and exit ends removed.
FIGS. 12C and 12D show replaceable filter units according to an embodiment.

FIGS. 12A-12D illustrate the disinfection chamber 100 with an attached HEPA filter unit 910 and a second filter unit 920. The housing 110 encloses multiple disinfection chambers 200. A rectangular entrance end 800 can be removed by unclamping two entrance clasps 802 and 804 on opposing sides of the top of the entrance end and lifting the end 800 out of the lipped shelf 815 that holds the bottom of the entrance end. Held within the inner framework of the entrance end 800 is a High Efficiency Particulate Air filter (i.e., HEPA) filter 910. Once the entrance end 800 has been removed from the device, a fitted HEPA filter can be fitted within the inner framework. The embodiment of the HEPA filter shown in FIG. 12D is sized to fit snugly into the inner framework of the entrance end 800. The HEPA filter 910 fits over the housing inlet 115 so that the incoming air flow 970 (e.g., ambient air, recirculated air, or some other processed air stream) enters one end of the HEPA filter. Once it enters the HEPA filter, the filter the air path 972 flows throughout the HEPA filter in a serpentine fashion around a number of partitions 915. This serpentine filtration path increases the efficiency of the filtration process.

Similarly, the rectangular exit end 805 can be removed by unclamping two exit clasps 807 and 809 on opposing sides of the top of the exit end and lifting the exit end 805 out of the lipped shelf 817 that holds the bottom of the exit end. Held within the inner framework of the exit end 805 is a second filter unit 920. One embodiment of the second filter unit 920 is an activated charcoal filter. The second filter unit may include one or more types of filters, laser beams, electric current, ultrasound, and mixtures thereof. Once the exit end has been removed from the device a new second filter unit 920 can be fitted within the inner framework. The embodiment of the second filter unit 920 shown in FIG. 12C is sized to fit snugly into the inner framework of the exit end 805. The second filter unit faces the outlet end of the housing so that the purified and disinfected air flow enters an entry port 925 at one end of the second filter unit. Once it enters the second filter unit, the air path 982 flows throughout the second filter unit in a serpentine fashion around a number of partitions 923 as shown in FIG. 12C until the filtered purified and disinfected air stream 980 exits the filter outlet 927. The serpentine path through this second filter unit 920 increases the efficiency of the filtration process.

Figure 13:
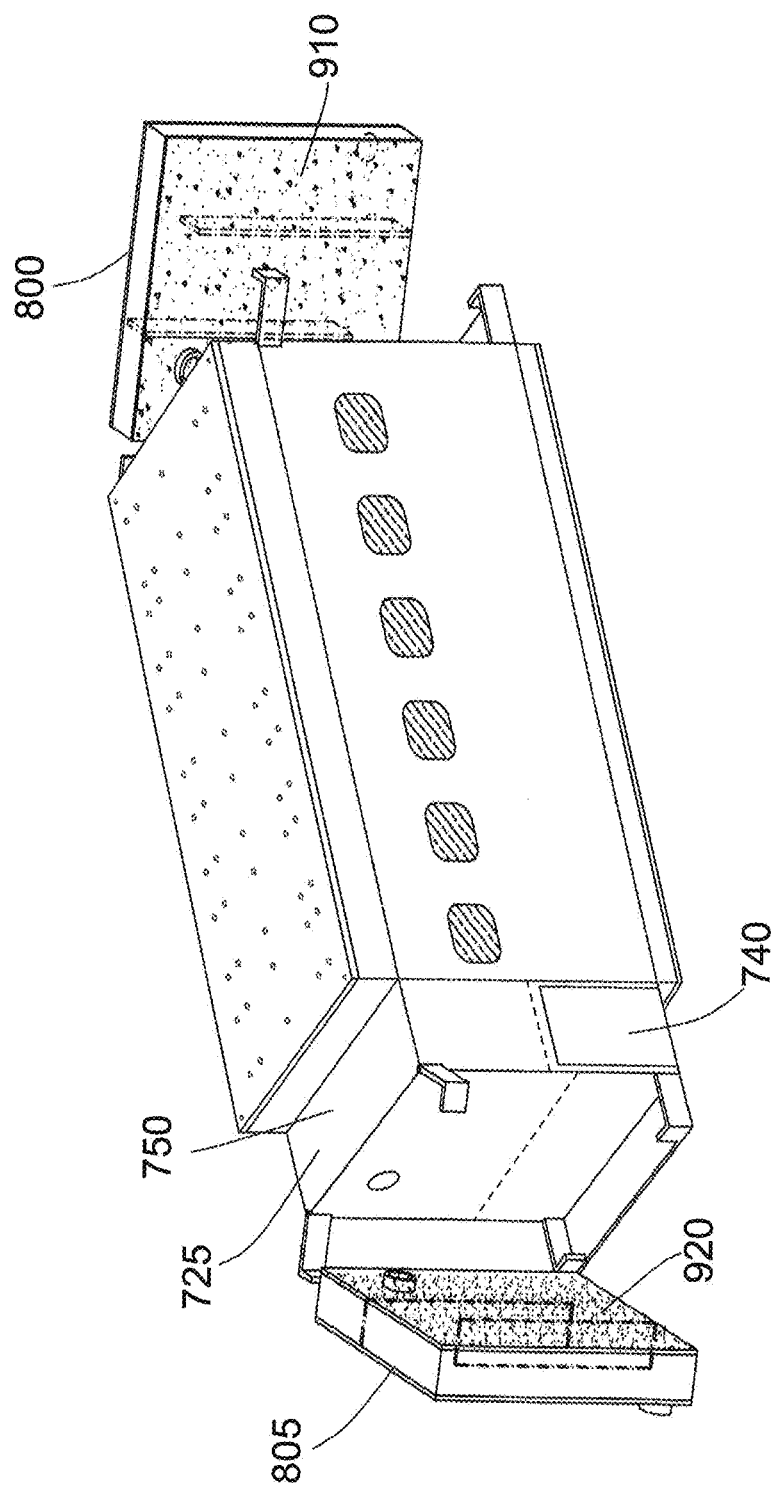
FIG. 13 illustrates the air disinfection device shown in FIG. 2 interconnected with an air mover module and a first and second filter unit on opposing ends of the device according to an embodiment.

FIG. 13 shows an embodiment similar to that shown in FIG. 12A but having an air mover module 750 inserted between the outlet end of the disinfection module 100 and the second filter unit 920. The air mover module has a power supply 740 and a pump 725.

FIG. 14 shows an air purification and disinfection system 500 wherein the housing 510 may have a number of different shapes or configurations. In FIG. 14 the housing 510 has an extension off the rectangular portion of the housing. The housing inlet 515 and the housing outlet 517 are not on opposed sides of the housing 510. Instead, the housing inlet is on one end of the housing 510 and the housing outlet is located within an extension 520.

On either end of the UV-C chambers, additional disinfection chambers may be added to meet the needs of any special situation. For instance, the smallest personal unit can be with an air purification module with a single air chamber, while larger air conditioner units may have a dozen or more disinfection modules, each module having multiple disinfection chambers. The modules being interconnected using serial connections like Lego pieces. Each chamber will still have the helical air diverter to force a circular path and create a centrifugal force for the air flow. By creating the inlet and the outlet of the chambers at the opposite ends, a lengthy circular air passage is ensured whether it is through one chamber or multiple chambers. The resulting centrifugal force and the double serpiginous passage of air will ensure close contact between any microorganisms or pathogens and the UV-C light for a prolonged and adequate time.

Depending upon the specific need, the unit can have an AC connection or a rechargeable battery provision. The rechargeable battery can also be replaceable. The unit also comes with an optional pump to control the speed of air passage through the unit. It is especially needed in a personal unit, where the required air flow per minute for breathing should be adjustable. The pump can also work intermittently to coincide with the inspiration of the breath cycle remaining in an off position during the expiration.

One aspect of the "expandable" feature of the system is that it can comprise any number of modules. For example, the system may have multiple filter modules, multiple disinfection modules, and multiple air mover modules. The modules may be interconnected in a variety of ways, such as one air disinfection and purification system similar to that shown in FIG. 12B connected by a hose (not shown) to another similar system or to any selection of additional modules. The "expandable" feature also includes one or more of the following: 1) a variable number of septations in the HEPA/ultra filter and variations in the size of the filter to increase efficiency; 2) a variable number of septations in the activated charcoal filter and variations in its size to increase efficiency; 3) a variable number of UV-C chambers from one to as many as needed; 4) a variable number of discs or rungs in the helical diverter; 5) an increase or decrease in the diameter of the helical diverter discs; 6) variation in the overall size of the system to plan for an individual user or to plan for the system's use in a full air conditioning system; and 7) the use of one or more air mover modules to adjust the air flow speed.

While the foregoing describes various embodiments of the invention, additional embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

I claim:
1. An air disinfection module comprising:
 (a) a UV-C opaque housing having a housing inlet and a housing outlet; and
 (b) a disinfection chamber within the opaque housing having:
  (i) UV-C transparent walls,
  (ii) a centralized inner bore,
  (iii) an interior chamber surface facing the inner bore;
  (iv) one or more UV-C light sources positioned adjacent the interior chamber surface, wherein the one or more UV-C light sources are arranged around the periphery of the disinfection chamber;
  (v) a helical air flow diverter centralized within the inner bore proximate to the one or more UV-C light sources, wherein the helical air flow diverter creates a helical and serpentine pathway for air with pathogens as the air moves from the housing inlet to the housing outlet, and wherein centrifugal forces caused by the air flowing through the helical air flow diverter facilitates a close contact between the pathogens and the one or more UV-C light sources arranged around the periphery of the disinfection chamber.

2. The air disinfection module as claimed in claim 1, further comprising a first replaceable filter having a plurality of septations creating a serpentine airflow pathway going from a filter inlet to a filter exit.

3. The air disinfection module as claimed in claim 2, further comprising a second replaceable filter.

4. The air disinfection module as claimed in claim 3, wherein the second replaceable filter is an activated carbon filter.

5. The air disinfection module as claimed in claim 2, wherein the first replaceable filter is a HEPA filter.

6. The air disinfection module as claimed in claim 1, wherein a portion of the interior chamber surface comprises a reflective surface coated with titanium dioxide.

7. The air disinfection module as claimed in claim 1, wherein the helical air flow diverter has a rough surface, or a reflective surface coated with titanium dioxide.

8. The air disinfection module as claimed in claim 1, further comprising a top and a bottom ballast, wherein the one or more UV-C light sources are attached to the top and the bottom ballast.

9. The air disinfection module as claimed in claim 1, further comprising a removable end connected to the housing inlet or the housing outlet.

10. The air disinfection module as claimed in claim 1, further comprising an air mover unit, wherein the air mover controls a rate of air flow through the module.

11. The air disinfection module as claimed in claim 1, wherein the opaque housing has a UV-C opaque inspection window to monitor the operation and viability of the components of the disinfection chamber and allow an operator of the device to access the interior of the disinfection chamber.

12. The air disinfection module as claimed in claim 1, wherein the helical air flow diverter comprises a plurality of undetachable radial extensions or slanted partitions along its surface.

13. An air purification and disinfection system comprising a:
  (a) an air mover unit, wherein the air mover controls a rate of air flow through the system;
  (b) a collection of two or more air disinfection units housed inside UV-C opaque housing, the UV-C opaque housing having a housing inlet and a housing outlet, each air disinfection unit having a disinfection chamber comprising:
    (i) UV-C transparent walls,
    (ii) a centralized inner bore,
    (iii) an interior chamber surface facing the inner bore;
    (iv) one or more UV-C light sources positioned adjacent the interior chamber surface, wherein the one or more UV-C light sources are arranged around the periphery of the disinfection chamber;
    (v) a helical air flow diverter centralized within the inner bore proximate to the one or more UV-C light sources, wherein the helical air flow diverter creates a helical and serpentine pathway for air with pathogens as the air moves from the housing inlet to the housing outlet, wherein centrifugal forces caused by the air flowing through the helical air flow diverter facilitates a close contact between the pathogens and the one or more UV-C light sources arranged around the periphery of the disinfection chamber; and
  (c) a first replaceable filter having a plurality of septations creating a serpentine airflow pathway going from a filter inlet to a filter exit.

14. The system as claimed in claim 13, further comprising a second replaceable filter.

15. The system as claimed in claim 14, wherein the second replaceable filter is an activated carbon filter.

16. The system as claimed in claim 14, wherein the first and the second replaceable filter are at opposed ends of the system.

17. The system as claimed in claim 13, wherein the first replaceable filter is a HEPA filter.

18. The system as claimed in claim 13, wherein the housing has a UV-C opaque inspection window to monitor the operation and viability of the components of the disinfection chamber and allow an operator of the device to access the interior of the disinfection chamber.

19. The air purification and disinfection system as claimed in claim 13, wherein a first air disinfection unit of the two or more air disinfection unit is interconnected to a second air disinfection unit of the two or more air disinfection unit, wherein an outlet of the first air disinfection unit is connected to an inlet of the second air disinfection unit such that disinfected air flows from the outlet of the first air disinfection unit and enters the inlet of the second air disinfection unit for further disinfection.

20. The air purification and disinfection system as claimed in claim 19, wherein the first air disinfection unit is interconnected to the second air disinfection unit using bellows.

21. The air purification and disinfection system as claimed in claim 20, wherein the bellows ensures passage of disinfected air from the first air disinfection unit into the interconnected second air disinfection unit.

22. The air purification and disinfection system as claimed in claim 19, wherein air disinfection is carried out in a graded and predictable manner by regulating:
  (i) the intensity, quantity, and placement of the one or more UV-C light sources in each disinfection chamber; and
  (ii) the number of air disinfection units in the system.

* * * * *